US008093435B2

(12) United States Patent
Chiba et al.

(10) Patent No.: US 8,093,435 B2
(45) Date of Patent: Jan. 10, 2012

(54) REAGENT FOR ORGANIC SYNTHESIS AND METHOD OF ORGANIC SYNTHESIS REACTION WITH THE REAGENT

(75) Inventors: Kazuhiro Chiba, Fuchu (JP); Shokaku Kim, Koganei (JP); Yusuke Kono, Koganei (JP)

(73) Assignee: JITSUBO Co., Ltd., Tokyo (JP)

( * ) Notice: Subject to any disclaimer, the term of this patent is extended or adjusted under 35 U.S.C. 154(b) by 61 days.

(21) Appl. No.: 12/225,442

(22) PCT Filed: Feb. 19, 2007

(86) PCT No.: PCT/JP2007/052996
§ 371 (c)(1),
(2), (4) Date: May 18, 2009

(87) PCT Pub. No.: WO2007/122847
PCT Pub. Date: Nov. 1, 2007

(65) Prior Publication Data
US 2009/0299103 A1 Dec. 3, 2009

(30) Foreign Application Priority Data

Mar. 24, 2006 (JP) ................. 2006-084019

(51) Int. Cl.
*C07C 43/205* (2006.01)
*C07C 321/06* (2006.01)
*C07C 217/58* (2006.01)
*C07C 217/60* (2006.01)
*C07C 217/62* (2006.01)
(52) U.S. Cl. ........... 568/648; 568/62; 564/374; 564/389
(58) Field of Classification Search ........................ None
See application file for complete search history.

(56) References Cited

U.S. PATENT DOCUMENTS 4,014,937 A * 3/1977 Richardson .................. 564/374

FOREIGN PATENT DOCUMENTS

| EP | 1426101 | 6/2004 |
|---|---|---|
| EP | 1621249 | 2/2006 |
| JP | H06-239995 | 8/1994 |
| JP | 2000/44493 | 2/2000 |
| JP | 2001/122889 | 5/2001 |
| JP | 2003/183298 | 7/2003 |
| JP | 2003-292494 | 10/2003 |
| JP | 2004-059509 | 2/2004 |
| JP | 2005-29479 | 2/2005 |
| JP | 2005-508890 | 4/2005 |
| WO | 97/42166 | 11/1997 |
| WO | 03/016246 | 2/2003 |
| WO | 03/018188 | 3/2003 |
| WO | 2006/104166 | 10/2006 |

OTHER PUBLICATIONS

Hayashi K. et al., "Microwave-promoted Suzuki-Miyaura coupling reactions in a cycloalkane-based thermomorphic biphasic system", Tetrahedron Letters 47, 2006, pp. 171-174.
Azefu Y. et al., "Facile Synthesis of Stable Lipid Analogues Possessing a Range of Alkyl Groups: Application to Artificial Glycolipids", Bioorganic & Medicinal Chemistry, 10, 2002, pp. 4013-4022.
Sato R. et al., "Synthesis of 3, 4, 5-Tris (alkyloxy) benzyl Glycosides as Glycolipid Analogues", Journal of Carbohydrate Chemistry, vol. 23, No. 6&7, 2004, pp. 375-388.
Martinez-Palau M. et al., "Synthesis of Luminescent N-Arylcarbazoles by Copper Bronze-Mediated Reaction", Letters in Organic Chemistry, 2004, vol. 1, No. 3, pp. 231-237.
Tamiaki H. et al., "A Novel Protecting Group for Constructing Combinatorial Peptide Libraries", Bull. Chem. Soc. Jpn., 74, 2001, pp. 733-738.
Chiba K. et al., "A liquid-phase peptide synthesis in cyclohexane-based biphasic thermomorphic systems", Chem. Commun., 2002, pp. 1766-1767.
Yamaguchi T. et al., "Macroscopic Spinning Chirality Memorized in Spin-Coated Films of Spatially Designed Dendritic Zinc Porphyrin J-Aggregates", Angew. Chem. Int. Ed., 2004, 43, pp. 6350-6355.
Kishimura A. et al., "Phosphorescent Organogels via 'Metallophilic' Interactions for Reversible RGB-Color Switching", J. Am. Chem. Soc., 2005, vol. 127, No. 1, pp. 179-183.
Misawa et al, "An Isothiouronium-derived Organized Monolayer at the Air-Water Interface: Design of Film-based Anion Sensor Systems for H2PO4-," Chemistry Letters, vol. 33, No. 9 (2004), pp. 1118-1119.
Jurgen Sleven et al.: "Synthesis, spectral and mesomorphic properties of octa-alkoxy substituted phthalocyanine ligands and lanthanide complexes" Materials Science and Engineering, vol. C18, 2001, pp. 229-238, XP002553678. Virgil Percec et al.: "Coassembly of a hexagonal columnar liquid crystalline superlattice from polymer(s) coated with a three-cylindrical bundle supramolecular dendrimer" Chem. Eur. J., vol. 5, No. 3, 1999, p. 10701083, XP002553679.
Myongsoo Lee et al.: "Synthesis and mesomorphic properties of palladium(II) complexes based on 3,4,5-trialkoxy benzonitrile ligands" Bull. Korean Chem. Soc., vol. 18, No. 10, 1997, pp. 1067-1070, XP002553680.
Egbe D A M et al: "Synthesis and Properties of Novel Well-Defined Alternating PPE/PPV Copolymers" Macromolecular Chemistry and Physics, Wiley-VCH Verlag, Weinheim, DE, vol. 202, No. 13, Jan. 1, 2001, pp. 2712-2726, XP001179996 ISSN: 1022-1352.
Daniel Ayuk Mbi Egbe et al.: "Influence of the conjugation pattern on the photophysical properties of alkoxy-substituted PE/PV hybrid polymers" Macromolecules, vol. 36, 2003, pp. 9303-9312, XP002553681.

(Continued)

Primary Examiner — Brian J Davis
(74) Attorney, Agent, or Firm — Dorsey & Whitney LLP

(57) ABSTRACT

A reagent for organic synthesis with which a chemical reaction can be conducted in a liquid phase and unnecessary compound(s) can be easily separated at low cost from the liquid phase after completion of the reaction. The reagent for organic synthesis reversibly changes from a liquid-phase state to a solid-phase state with changes in solution composition and/or solution temperature, and is for use in organic synthesis reactions. This reagent for organic syntheses facilitates process development. With the reagent, research on and development of, e.g., medicines through, e.g., compound library synthesis, etc. can be accelerated. It can hence contribute to technical innovations in the biochemical industry and chemical industry.

3 Claims, No Drawings

OTHER PUBLICATIONS

Daniel Ayuk Mbi Egbe te al.: "Odd-even effects and the influence of length and specific positioning of alkoxy side chains on the optical properties of PPE-PPV polymers" Chem. Mater., vol. 17, 2006, pp. 6022-6032, XP002553682.

European Search Report issued to European Application No. 07714522.5, mailed Dec. 7, 2009.

Decision of Refusal issued to JP Application No. 2008-511981, mailed Jun. 23, 2009.

Rolf Schmidt et al: "New bisamides gelators: relationship between chemical structure and fiber morphology" Tetrahedron Letters 44 (2003) 3171-3174.

Office Action issued to Chinese Application No. 200780010322.2, mailed May 14, 2010.

* cited by examiner

REAGENT FOR ORGANIC SYNTHESIS AND METHOD OF ORGANIC SYNTHESIS REACTION WITH THE REAGENT

TECHNICAL FIELD

The present invention relates to a reagent for organic synthesis and a method of organic synthesis reaction using this reagent, and in more detail, it relates to a reagent for organic synthesis which is a compound which rapidly changes from a liquid phase state to a solid phase state due to a change in solution composition and/or solution temperature, which is provided as a compound acting as a reaction substrate or a catalyst in an organic synthesis reaction, or which is provided as a compound which bonds to unreacted compounds or byproducts in an organic synthesis reaction, which can be easily removed from the reaction system after the reaction; and to a method of organic synthesis using this reagent.

BACKGROUND ART

In chemical reaction processes, methods of separating as a solid a specified component dissolved in a liquid are widely used. This is because, by solidifying (crystallizing) only the specified component, separation and/or purification after the reaction are simplified. In particular, recently, in successive multistage synthesis such as compound library synthesis and the like used in the research and development of pharmaceuticals, after the completion of each reaction, by solidifying (crystallizing) the unnecessary compounds, the removal of the solidified (crystallized) substances becomes easy, and it is possible to prevent the processes from becoming complicated.

The solidification (crystallization) of specified components dissolved in a solution in this way is implemented by satisfying defined conditions in the relationship with chemical properties and physical properties of the compounds, and with the solvent.

However, the conditions for solidification (crystallization), in many cases, must be found by experience based on trial and error. Especially, in successive multistage synthesis, because it is necessary to consider the solidification (crystallization) conditions based on the characteristic properties of the compounds synthesized in each of the stages, process development is very expensive and time consuming.

In order to solve such problems, in the prior art, there was known a means of using a chemically modified reagent on polystyrene or silica, and separating the liquid including the products, and the reagents, by filtration after the reaction. With these reagents, it is possible to easily separate unreacted compounds added in excess, byproducts, and catalysts, in an organic synthesis reaction or the like, without complicated separation processes.

Further, Patent Document 1 discloses a method for practicing a nucleophilic substitution reaction (Mitsunobu reaction) of an alcohol for producing a desired product, including a step of reacting an alcohol and a nucleophilic reagent with an azodicarboxylate and a phosphine, wherein at least one of the azodicarboxylate and phosphine include at least one fluorous tag (a retention group of a highly fluorinated alkyl group or the like). Here, for example, fluorous solvents including perfluorocarbon or the like, will be present as a third phase without mixing with organic solvents or water, and have the characteristic of dissolving compounds having a fluorous tag.

Because of this, by adding a fluorous solvent to a uniform reaction phase, it is possible to easily separate a compound which must be separated from the product, and which has a fluorous tag.

Further, by using a fluorous carrier which selectively bonds to a fluorous tag, it is possible to easily separate a compound having a fluorous tag by solid-liquid extraction.

Patent Document 1: Japanese Publication No. 2005-508890 of PCT Application.

DISCLOSURE OF THE INVENTION

Problems to be Solved by the Invention

However, in the case of utilizing a reaction using a chemically modified reagent on polystyrene or silica, for the reagent carried on the polystyrene or silica, the reaction point is only at the solid liquid interface, thus the reactivity is often low. Further, there was the problem that it was not possible to use this method in many synthesis reactions where a product is produced by the reaction from sterically plural directions, two or more reagents, because the reaction was carried out on a solid surface.

Further, in the method disclosed in Patent Document 1, in the case of using a fluorous solvent when separating a compound having a fluorous tag, there was the problem that the costs of the reaction could not be kept low because fluorous solvents are expensive. Further, in the case of using a fluorous carrier in the separation of a compound having a fluorous tag, in addition to using an expensive fluorinated silica gel or the like, the separation operation is complex and cannot be easily used.

The present invention was made in view of the above problems, and has the objective of providing a reagent for organic synthesis and a method of organic synthesis reaction using the reagent, whereby a chemical reaction can be carried out in a liquid phase, and further, the separation of the unnecessary compounds from the liquid phase after the completion of the reaction can be carried out easily and also at low cost.

Means for Solving the Problems

The present inventors have carried out diligent research in order to solve the above problems. As a result, they arrived at and completed the present invention, discovering that by using a reagent for organic synthesis including an aromatic group having a specified hydrophobic group, and having a property of reversibly changing from a liquid phase state to a solid phase state according to changes in the solution composition and/or the solution temperature, it is possible to carry out the separation of unnecessary compounds from the liquid phase after the completion of the reaction, easily and furthermore, at low cost.

Specifically, the present invention provides the following.

The first aspect of the invention provides a reagent for organic synthesis which can be used for organic synthesis reactions, shown in the below Chemical Formula (1), having a property of reversibly changing from a liquid phase state to a solid phase state according to changes in solution composition and/or solution temperature.

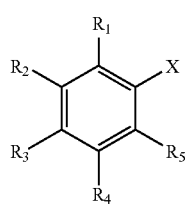

(1)

(In the formula, $R_1$ to $R_5$ may be the same or different, and represent hydrogen, halogen, or alkyl group with a carbon number of 1 to 30 which may have a substituent group, alkoxyl group with a carbon number of 1 to 30 which may have a substituent group, aryl group with a carbon number of 1 to 30 which may have a substituent group, acyl group with a carbon number of 1 to 30 which may have a substituent group, thioalkyl group with a carbon number of 1 to 30 which may have a substituent group, dialkylamino group with a carbon number of 1 to 30 which may have a substituent group, nitro group or amino group, and at least two of $R_1$ to $R_5$ are alkyl group with a carbon number of 18 to 30 which may have a substituent group, alkoxyl group with a carbon number of 18 to 30 which may have a substituent group, acyl group with a carbon number of 18 to 30 which may have a substituent group, thioalkyl group with a carbon number of 18 to 30 which may have a substituent group, or dialkylamino group with a carbon number of 18 to 30 which may have a substituent group. Further, in the formula, X represents a reagent active site having one or more atoms selected from the group consisting of a carbon atom, oxygen atom, sulfur atom, and nitrogen atom.)

According to the reagent for organic synthesis according to the first aspect, in addition to having a reagent active site having one or more atoms selected from the group consisting of carbon, oxygen, sulfur, or nitrogen atoms, it also has, as substituent groups on the aromatic ring, at least two of: alkyl group with a carbon number of 18 to 30 which may have a substituent group, alkoxyl group with a carbon number of 18 to 30 which may have a substituent group, acyl group with a carbon number of 18 to 30 which may have a substituent group, a thioalkyl group with a carbon number of 18 to 30 which may have a substituent group, or a dialkylamino group with a carbon number of 18 to 30 which may have a substituent group. Because of this, the reagent for organic synthesis can be dissolved uniformly with high concentration in many organic solvents, and it can react with a high degree of reactivity with other compounds in many organic solvents.

Further, the reagent for organic synthesis according to the first aspect can also be used mainly as a nucleophilic scavenger, electrophilic scavenger, synthesis building block, reaction accelerator, condensation agent, or metal ligand. Namely, it can be used in a wide range of applications, as a reaction substance for unnecessary substances such as byproducts, catalysts, and unreacted reaction substrate and the like, as a reaction substrate in an organic synthesis reaction, and as a catalyst or reaction accelerator in an organic synthesis reaction, and in addition, it has the property of reversibly changing from a liquid phase state to a solid phase state according to changes in solution composition and/or solution temperature, and thus can be easily separated from the reaction system by solidification after the reaction.

In this way, any compounds added to a reaction system, and byproducts generated in the reaction system, can be easily separated from the reaction system, or a specified reaction substrate or reaction accelerator can be added to the reaction system as a compound which can be easily separated later, and can be easily separated from the reaction system after the completion of the reaction.

Further, in a reaction using the reagent for organic synthesis of the first aspect, the organic synthesis reaction can be carried out at low cost without using particularly expensive reagents.

Here, the "reagent for organic synthesis" indicates all reagents used for carrying out organic synthesis reactions, or processes after the reaction, and includes reaction substrates, reaction accelerators, and synthesis building blocks, and the like. The reagent for organic synthesis according to the present invention is not particularly limited in terms of the amount used, and can be used in any case such as the case of use in large industrial quantities, or the case of use in small quantities for testing, research or the like. In the present invention, in particular, the compound has a structure such as that shown in Chemical Formula (1).

Further, the "reagent for organic synthesis" of the present invention has a "hydrophobic carrier group" as a portion thereof. In the present invention, "hydrophobic carrier group" indicates, in the compound (I), a site having a hydrophobic group, and specifically, in the Chemical Formula (1), indicates a portion excluding the reagent active portion which is X.

Further, "nucleophilic scavenger" indicates a compound which can bond to excess electrophilic reagents remaining unreacted with other reaction substrate substances among electrophilic reagents used a chemical reaction, and to compounds having electrophilicity which are produced as reaction byproducts, and further to unreacted reaction substrate.

The term "electrophilic scavenger" indicates a compound which can bond to excess nucleophilic reagents remaining unreacted with other reaction substrate substances among nucleophilic reagents used in a chemical reaction, and to compounds having nucleophilicity which are generated as reaction byproducts, and further to unreacted reaction substrate.

The term "synthesis building block" indicates an intermediate provided for the organic synthesis reaction of the desired compound in the present invention, and indicates a general term for a compound which can impart an arbitrary reagent activity to a reaction substrate by introducing a specified functional group via chemical bonding in an arbitrary reaction substrate.

The term "condensation agent" indicates a compound which acts to accelerate a dehydration condensation reaction by accelerating the elimination of active hydrogen and hydroxyl groups from a reaction substrate in a dehydration condensation reaction such as an ester synthesis reaction, amide synthesis reaction, ether synthesis reaction or the like.

The term "metal ligand" indicates a compound having an atomic group which can coordinate and bond to a metal ion added as a catalyst or reaction accelerator in an organic synthesis reaction.

Further, "reaction accelerator" indicates a compound which can accelerate an organic synthesis reaction by addition to a reaction system, and for example, acids, bases, catalysts and the like can be mentioned.

The second aspect of the invention provides a reagent for organic synthesis according to the first aspect, characterized in that, in Chemical Formula (1), X is a functional group shown by (A) to (M), or (A') to (M') below.

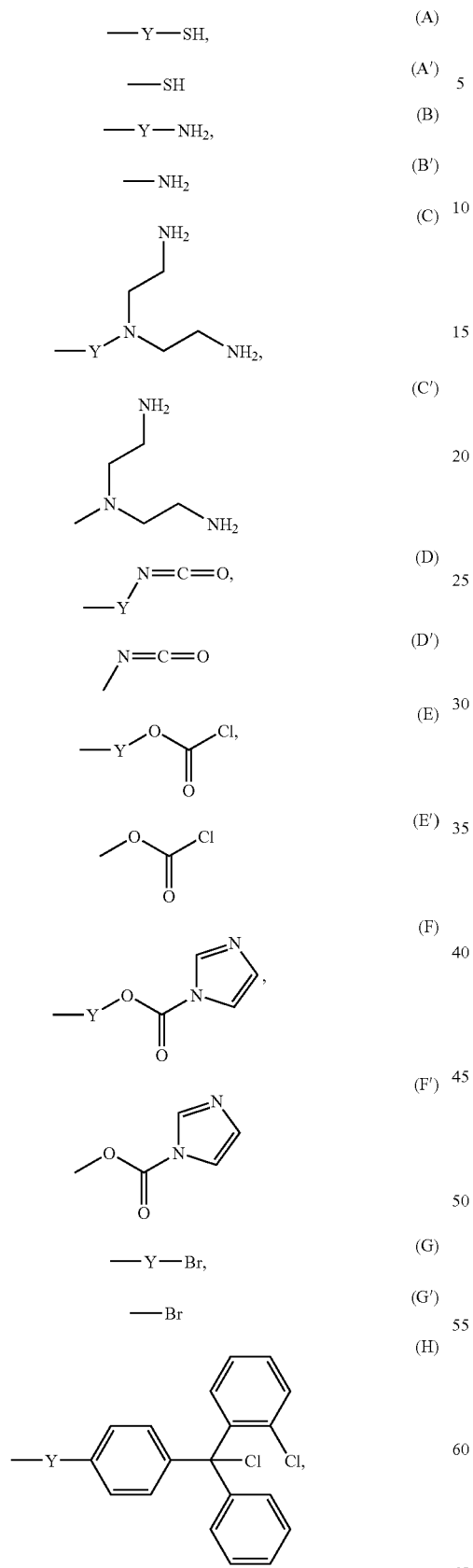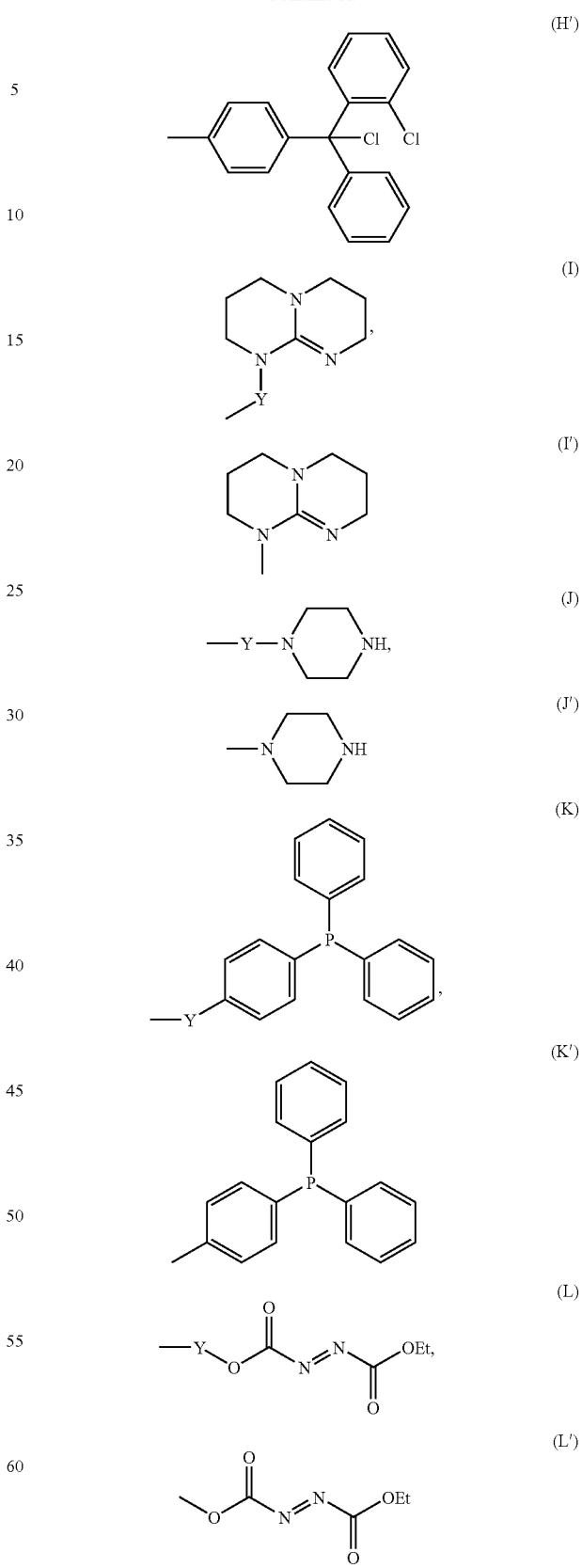

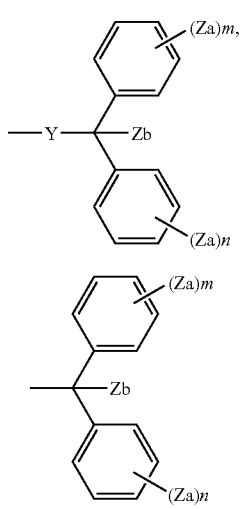

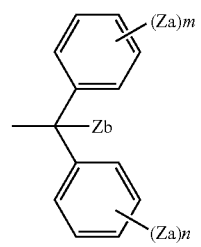

(In the formulas (A) to (M), Y is an ester bond, ether bond, amide bond, thioester bond, sulfide bond, urea bond, carbamate bond, or carbonate bond, or an alkylene group with a carbon number of 1 to 10 which may have such bonds. Further, in formulas (M) and (M'), m and n are independently 0 or 1, Za is a chlorine atom or a bromine atom, Zb is a hydroxyl group, chlorine atom, or a bromine atom.)

Here, a "carbamate bond" is the chemical bond shown in Chemical Formula (N).

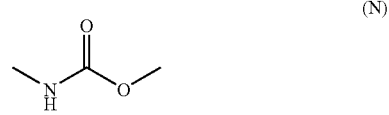

Further, a "carbonate bond" is the chemical bond shown in Chemical Formula (O).

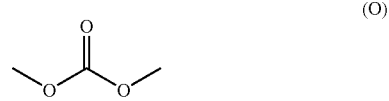

The reagent for organic synthesis of the second aspect can be used for the following applications. Namely, in the case that among the compounds (1) indicated in the second aspect, X is reagent active site shown by the Chemical Formula (A) to (C) or (A') to (C'), because it has a reaction center having nucleophilicity, such as a thiol group, amino group, or the like, it can be used as a nucleophilic scavenger.

Further, in the case that among the compounds (1) shown in the second aspect, X is a reagent active site indicated by the Chemical Formulas (D) to (H), or (D') to (H'), because it has a reaction center having electrophilicity, such as a carbonyl carbon atom, or the like, it can be used as an electrophilic scavenger. Further, also in the case that among the compounds (1), X is a reagent active site shown by the Chemical Formulas (M), or (M'), because the carbon atom to which a hydroxyl group is bonded, and the carbon atom to which a halogen atom, not directly bonded to a benzene ring, is bonded have electrophilicity, it can be used as an electrophilic scavenger.

Moreover, in the case that among the compounds (1) indicated in the second aspect, X is a reagent active site shown by the Chemical Formulas (A) to (H), or (A') to (H'), because structural changes for a compound having arbitrary reagent activity are possible via a sulfide bond, thioester bond, amino bond, amide bond, carbamate bond, urea bond, carbonate bond, ether bond, or ester bond, it can also be used as a synthesis building block.

In the case that among the compounds (1) indicated in the second aspect, X is a reagent active site shown by the Chemical Formulas (I), (J), (I') or (J'), because an amino group or the like shows strong basicity, it can be used as a reaction accelerator as a strong base. Namely, these compounds, as strong bases, by capturing active hydrogen of one portion of the reaction substrate, can be used as reaction accelerators for nucleophilic reactions, deprotecting reactions, esterification reactions of carboxylic acids, alkylation reactions of active methylenes, alkylation reactions of amines, alkylation reactions of phenols, alkylation reactions of thiols, and the like.

In the case that among the compounds (1) indicated in the second aspect, X is a reagent active site shown by the Chemical Formulas (K), or (K'), the unbonded electron pair of the phosphorous atom is donated to a metal atom, and in addition, an electron pair is back-donated from the metal atom to the π orbital of the tertiary phosphine. Because of this, these compounds can form strong coordination bonds with metal atoms.

Further, in the case that among the compounds (1) indicated in the second aspect, X is a reagent active site shown by the Chemical Formulas (K), (L), (K'), or (L'), because (K) or (K') act in the same way as triphenylphosphine, and further, because (L) or (L') act in the same way as diethyl azodicarboxylate, these can be used as condensation agents for many condensation reactions publicly known as Mitsunobu reactions.

The third aspect of the invention provides a reagent for organic synthesis according to the first or second aspect, wherein in the Chemical Formula (1), $R_2$ and $R_4$ are a docosyloxy group ($C_{22}H_{45}O$—), and $R_1$, $R_3$ and $R_5$ are hydrogen.

Because the reagent for organic synthesis according to the third aspect has two docosyloxy groups, it can be dissolved uniformly at high concentration in many organic solvents, and it can react with a high degree of reactivity with other compounds in many organic solvents.

The fourth aspect of the invention provides a reagent for organic synthesis according to the third aspect, wherein in the Chemical Formula (1), the reagent active site X is a functional group shown by the formula (M) or (M').

The reagent for organic synthesis according to the fourth aspect is, specifically, the compound shown by Chemical Formula (2a).

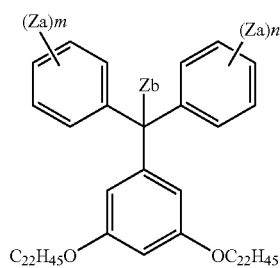

(In Formula (2a), m and n are independently 0 or 1, Za is a chlorine atom, or bromine atom, Zb is a hydroxyl group, chlorine atom, or bromine atom.)

Because the reagent for organic synthesis according to the fourth aspect has a hydroxyl group, chlorine atom, or bromine atom, it can be used as an electrophilic scavenger. Further, because the reagent for organic synthesis according to the fourth aspect has two docosyloxy groups, it can be dissolved uniformly at high concentration in many organic solvents, and it can react with a high degree of reactivity with other compounds in many organic solvents.

The fifth aspect of the invention provides a reagent for organic synthesis according to the first aspect, wherein in the Chemical Formula (1), the reagent active site X is a hydroxymethyl group, and $R_2$ and $R_4$ are a docosyloxy group ($C_{22}H_{45}O-$), and $R_1$, $R_3$ and $R_5$ are hydrogen.

In other words, the invention according to the fifth aspect is a reagent for organic synthesis shown by the following Chemical Formula (2) which can be used for organic synthesis.

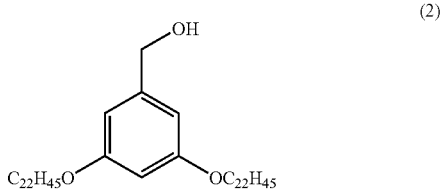

(2)

Because the reagent for organic synthesis according to the fifth aspect has a hydroxyl group, it can be used as an nucleophilic scavenger. Further, because the reagent for organic synthesis according to the fifth aspect has two docosyloxy groups, it can be dissolved uniformly at high concentration in many organic solvents, and it can react with a high degree of reactivity with other compounds in many organic solvents.

The sixth aspect of the invention provides a method of organic synthesis reaction using the reagent for organic synthesis according to any one of the first to fifth aspects, comprising a reaction step of carrying out a reaction wherein the reagent for organic synthesis is dissolved in a reaction system where the reagent active site X of Chemical Formula (1) participates in the reaction, and after this, a separation step of separating the reagent for organic synthesis and the reacted reagent for organic synthesis.

Taking note of the reagent for organic synthesis disclosed in the fifth aspect, the invention according to the sixth aspect is method of organic synthesis reaction using the reagent for organic synthesis according to the fifth aspect, comprising a reaction step of carrying out a reaction where the reagent for organic synthesis is dissolved in a reaction system where the hydroxyl group in Chemical Formula (2) participates in the reaction, and after this, a separation step of separating the reagent for organic synthesis and the reacted reagent for organic synthesis.

According to the method of organic synthesis reaction according to the sixth aspect, in the reaction step, it is possible to carry out a chemical reaction for producing the desired compound, using the reagent for organic synthesis according to any one of the first to fifth aspects. Further, because it is possible to separate, by the separation step, byproducts having a hydrophobic carrier group of the reagent for organic synthesis among the byproducts produced by the chemical reaction, and the reagent for organic synthesis added to the reaction system in excess and remaining unreacted, it is possible to easily carry out a procedure of separating other compounds from the desired compound.

Further, in the reaction step of the method of organic synthesis reaction according to the sixth aspect, it is also possible to add a reagent for organic synthesis in addition to any chemical reaction for obtaining the desired compound, and to react the reagent for organic synthesis with excess reaction substrate added in excess to the reaction system and byproducts.

Here, "method of organic synthesis reaction" indicates a method for producing by an organic synthesis reaction a desired compound, and in the present invention, in particular, it indicates a method using the reagent for organic synthesis disclosed in any of the first to fifth aspects. The method of organic synthesis reaction of the present invention is not particularly limited in the used amount of the reagent for organic synthesis, and can be carried out with any amount, such as the case of using the reagent for organic synthesis in large industrial amounts, or in the case of using small amounts in testing and research.

Further, the separation step in the method of organic synthesis reaction according to the sixth embodiment includes a step of crystallizing and separating the reagent for organic synthesis, and the reacted reagent for organic synthesis, by means of changing the solution composition and/or by means of changing the solution temperature. Namely, because the reagent for organic synthesis disclosed in any one of the first to fifth aspects reacts sharply to changes in solvent composition and/or solvent temperature, by using a means to change the composition and/or the temperature of the solvent, the reagent for organic synthesis or the reacted reagent for organic synthesis can be crystallized, and the reagent for organic synthesis and the reagent for organic synthesis after reaction can be easily crystallized and separated in a state where the desired compound of the synthesis remains in the solution.

As the means for changing the solution composition, for example, the means of adding another solvent to the reaction system, such as a poor solvent with respect to the reagent for organic synthesis, or the means of concentrating the solvent can be mentioned. As a means for changing the solution temperature, for example, the means of cooling the solution can be mentioned.

Effects of the Invention

According to the present invention, the reagent for organic synthesis can be uniformly dissolved in many organic solvents, and thus can be reacted with a high degree of reactivity with other compounds. Further, after the reaction, it is possible to choose from many separation methods such as a solid liquid separation method by crystallizing the reagent for organic synthesis, and the reacted reagent for organic synthesis, or a liquid liquid extraction method by adding a separation solvent which is immiscible with the reaction solvent, and partitioning the reagent for organic synthesis and the reacted reagent for organic synthesis into the separation solvent. Because the separation conditions of these separation methods can be uniformly determined based on the properties of the reagent for organic synthesis, it is not necessary to consider the separation conditions based on the characteristic properties or the like of each organic synthesis reaction. This not only simplifies process development, but also, for example, makes it possible to accelerate the research and development of pharmaceuticals and the like by compound library synthesis and the like, and this can in turn contribute to technical innovations in the biochemical industry and chemical industry.

Further, organic synthesis reactions using the organic synthesis reagent of the present invention do not use especially expensive compounds, and thus the organic synthesis reaction can be carried out at low cost.

PREFERRED MODE FOR CARRYING OUT THE INVENTION

Embodiments of the invention are described in detail below. These embodiments do not in any way limit the reagent for organic synthesis or the method of organic synthesis reaction using this reagent of the present invention, and appropriate modifications can be made within the scope of the objectives of the present invention.

Reagent for Organic Synthesis

The reagent for organic synthesis according to the present embodiment is shown by Chemical Formula (1) where $R_1$ to $R_5$ may be the same or different, and represent a hydrogen, halogen, alkyl group, alkoxyl group, aryl group, acyl group, thioalkyl group, or dialkylamino group with a carbon number of 1 to 30 which may have a substituent group; nitro group, or amino group, and at least two of $R_1$ to $R_5$ are alkyl group, alkoxyl group, acyl group, thioalkyl group, or dialkylamino group with a carbon number of 18 to 30 which may have a substituent group. Further, in the formula, X represents a reagent active site having at least one atom selected from the group consisting of carbon, oxygen, sulfur or nitrogen atom.

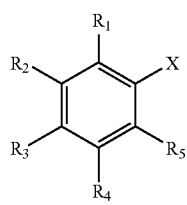

(1)

Because the above compound has at least two hydrophobic groups selected from the group consisting of alkyl group, alkoxyl group, acyl group, or thioalkyl group with a carbon number of 18 to 30 which may have a substituent group, it can show sufficient hydrophobicity, and can dissolve in a wide range of organic solvents, and further, a compound where the 3-position and 5-position with respect to X ($R_2$ and $R_4$) are substituted with an alkoxyl group with a carbon number of 18 to 30 is also stable with respect to acid treatment, and is especially suitable for the reagent for organic synthesis of the present invention.

Reagent Active Site

In the above Chemical Formula (1), X indicates a reagent active site having at least one atom selected from the group consisting of carbon, oxygen, sulfur, and nitrogen atom. Here, X may also have a structure indicated by the following Chemical Formulas (A) to (M), or (A') to (M'). Here, Y is an ester bond, ether bond, amide bond, amino bond, thioester bond, sulfide bond, urea bond, carbamate bond or a carbonate bond, or an alkylene group with a carbon number of 1 to 10 which may have one of these bonds. Further, in Formulas (M) and (M'), m and n are independently 0 or 1, Za is a chlorine atom or bromine atom, and Zb is a hydroxyl group, chlorine atom, or bromine atom.

—Y—SH, (A)

—SH (A')

—Y—NH₂, (B)

—NH₂ (B')

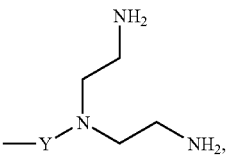

(C)

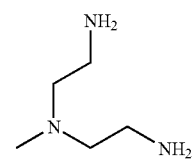

(C')

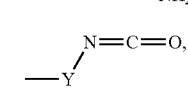

(D)

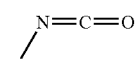

(D')

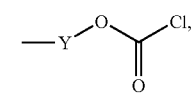

(E)

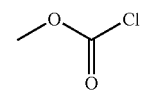

(E')

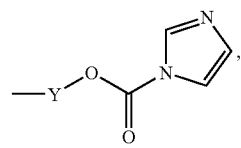

(F)

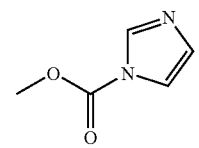

(F')

—Y—Br, (G)

—Br (G')

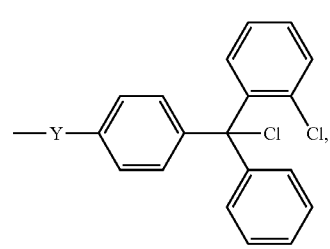

(H)

(H')

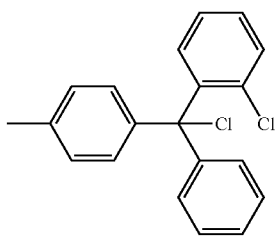

(I)

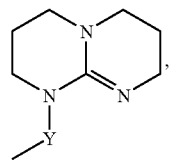

(I')

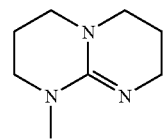

(J)

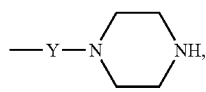

(J')

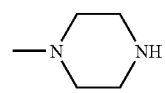

(K)

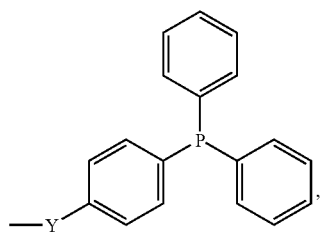

(K')

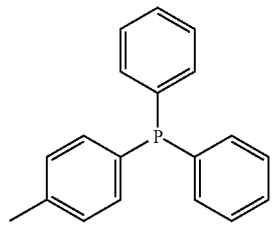

(L)

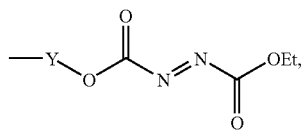

(L')

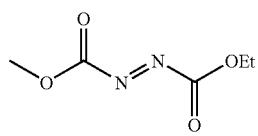

(M)

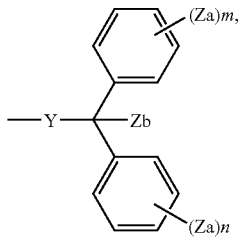

(M')

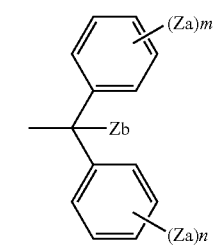

Further, in the reagent for organic synthesis of the present embodiment, a compound where $R_2$ and $R_4$ are docosyloxy groups ($C_{22}H_{45}O$—), and $R_1$, $R_3$ and $R_5$ are hydrogen is preferable.

Furthermore, the reagent for organic synthesis of the present embodiment may be a compound shown by the following Chemical Formula (2).

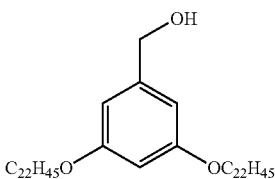

(2)

Namely, the compound shown by the Chemical Formula (2) is a reagent for organic synthesis shown by the Chemical Formula (1), wherein in the Chemical Formula (1), X is a hydroxymethyl group, $R_2$ and $R_4$ are docosyloxy ($C_{22}H_{45}O$—), $R_1$, $R_3$ and $R_5$ are hydrogen.

Here, the compound shown by the Chemical Formula (2) has a hydroxyl group, and because it shows nucleophilicity, it can be used as a nucleophilic scavenger.

Manufacturing Method of the Reagent for Organic Synthesis

The manufacturing method of the reagent for organic synthesis indicated in the above formula is not particularly limited, but it can generally be synthesized by various reactions such as the following.

A compound having a plurality of phenolic hydroxyl groups such as methyl gallic acid, and a long chain brominated alkyl are reacted in N,N-dimethylformamide, under basic conditions, to yield an aromatic compound having an alkoxy group. Next, an ester site is converted to the other substituting group to induce the desired compound by a functional group substitution by a publicly known means, or the aromatic compound is combine to a specially prepared reagent active site in an arbitrary bounded form to manufacture the reagent of the present embodiment.

Method of Organic Synthesis Reaction

The reagent for organic synthesis of the present embodiment can be used by the same method of use as the reagent used in the liquid phase organic synthesis reactions of the prior art which do not have a hydrophobic carrier group. Namely, in a state wherein the reaction substrate to be reacted is dissolved or dispersed in a solvent, a reagent for organic synthesis having a hydrophobic carrier group is added, and a reaction is carried out. Here, as the solvent used in the reaction system, it is possible to use a general organic solvent in the reaction, but because the reactivity is increased as the solubility of the reagent for organic synthesis in the solvent increases, it is preferable to select a solvent for which the solubility of the reagent for organic synthesis is high. Specifically, tetrahydrofuran, dichloromethane, diethylether, hexane, cyclohexane, N,N-dimethylformamide and the like are preferable, but it is not particularly limited to this. To confirm the progress of the reaction, the same methods used for general liquid phase organic synthesis reactions can be applied. Namely, thin layer silica gel chromatography, high speed liquid chromatography, and the like can be used to track the reaction.

Reaction Step

In the reaction step, by reacting a specified reaction substrate and the reagent for organic synthesis, or by using the reagent for organic synthesis as a reaction accelerator in a specified chemical reaction, it is possible to obtain the desired compound. Further, it is possible to carry out an arbitrary chemical reaction for obtaining the desired compound, and reacting residual reaction substrate added in excess to the reaction system, and byproducts, with the reagent for organic synthesis.

Use of the Reagent for Organic Synthesis as a Synthesis Building Block

In the case of using the reagent for organic synthesis as a synthesis building block, for example, consideration can be given to using the reagent for organic synthesis as a reaction substrate in a nucleophilic addition reaction, nucleophilic substitution reaction, dehydration condensation reaction, and the like. As a reagent for organic synthesis reaction which can be used in such a reaction, there is no particular limitation, and for example, in the reagent for organic synthesis shown in Chemical Formula (1), a reagent for organic synthesis where X is a reagent active site shown by (A) to (H) or (A') to (H') can be mentioned. As the solvent used for the reaction, any solvent which can be ordinarily used for these reactions can be used, and in the present embodiment, from the point of solubility of the reagent for organic synthesis having a hydrophobic carrier group, it is possible to use tetrahydrofuran, dichloromethane, cyclohexane/N,N-dimethylformamide mixed solvent and the like.

Use or the Reagent for Organic Synthesis as a Reaction Accelerator

The reagent for organic synthesis of the present embodiment can be used as a reaction accelerator. The effect as a reaction accelerator depends on the properties of the reagent active site of the reagent for organic synthesis, for example, the degree of acidity and basicity, the catalytic activity and the like. A reagent active site having such properties can be introduced on a hydrophobic carrier group by using a synthesis building block.

There is no particular limitation on the reagent for organic synthesis which can be used as a reaction accelerator, and for example, in the reagent for organic synthesis shown by Chemical Formula (1), a reagent for organic synthesis where X is a reagent active site shown by (I), (J), (I') or (J') can be mentioned. These reagents for organic synthesis show strong basicity, and by scavenging active hydrogens of the reaction substrate, can accelerate nucleophilic reactions, deprotecting reactions, esterification reactions of carboxylic acids, alkylation reactions of active methyl, alkylation reactions of secondary amines, alkylation reactions of phenols, and alkylation reactions of thiols.

Acceleration of Deprotecting Reactions

A reagent for organic synthesis having strong basicity can be used, for example, for the deprotecting reaction of an Fmoc group (9-fluorenylmethoxycarbonyl group), known as a protecting group of amino groups, and the like, but it is not particularly limited to these reactions. As the solvent used for the reaction, any one which can be ordinarily used for such reactions can be used, and in the present embodiment, from the point of solubility of the reagent for organic synthesis having a hydrophobic carrier group, it is possible to use tetrahydrofuran, dichloromethane, cyclohexane/N,N-dimethylformamide mixed solvent and the like.

The added amount of the reagent for organic synthesis used in the reaction can be appropriately set by one skilled in the art in consideration of the solubility of the reagent for organic synthesis in the used solvent, the equilibrium constant of the acid-base equilibrium of the basic groups, the reaction stoichiometry, and the like, and generally, it is preferable to add one to five times the theoretically required amount.

Further, a reagent for organic synthesis having a strong basicity, in the same was as its use as an accelerator or a deprotecting reaction, can be used as an accelerator of a nucleophilic reaction, deprotecting reaction, esterification reaction of a carboxylic acid, alkylation reaction of an active methylene, alkylation reaction of an amine, alkylation reaction of a phenol, alkylation reaction of a thiol, and the like. In these cases, it is possible to use the same solvent as the solvent used for a deprotecting reaction, and further, it is possible to accelerate the reaction by adding the reagent for organic synthesis in an amount which is the same as that of the reagent for organic synthesis used to accelerate deprotecting reactions.

Use of the Reagent for Organic Synthesis as a Condensation Agent

The reagent for organic synthesis of the present embodiment can be used as a condensation agent. For example, the reagent for organic synthesis can be used as condensation agent replacing the triphenylphosphine and diethyl azodicarboxylate required in the dehydration condensation reaction publicly known as the Mitsunobu reaction. As such a reagent for organic synthesis, for example, in the reagent for organic synthesis shown in Chemical Formula (1), a reagent for organic synthesis where X is a reagent active site shown by (K), (L), (K'), or (L') can be mentioned.

The dehydration condensation reaction which can be used in the present embodiment is not particularly limited, and for example, ester synthesis reactions, amide synthesis reactions and ether synthesis reactions can be mentioned. The solvent used for the reaction is not particularly limited if it is a solvent which can be ordinarily used for such reactions, and in the present embodiment, from the point of solubility of the reagent for organic synthesis having a hydrophobic carrier group, it is possible to use tetrahydrofuran, dichloromethane, cyclohexane/N,N-dimethylformamide mixed solvent and the like.

The added amount of the reagent for organic synthesis used in the reaction can be appropriately set by one skilled in the art in consideration of, for example, in the case of a Mitsunobu reaction, the solubility of the reagent for organic synthesis with respect to the used solvent, the stoichiometry of the Mitsunobu reaction, and the like, and in the case of adding the reagent for organic synthesis as a substitute substance of triphenylphosphine, it is preferable to add from 1 to 5 equivalents with respect to one equivalent of the dehydrated hydroxyl group, and in the case of adding as a substitute substance for diethyl azodicarboxylate, it is preferable to add from 1 to 5 equivalents with respect to one equivalent of the dehydrated hydroxyl group.

Use of the Reagent for Organic Synthesis as a Nucleophilic Scavenger and an Electrophilic Scavenger By using the reagent for organic synthesis of the present embodiment as a nucleophilic scavenger and an electrophilic scavenger, it is possible to capture electrophilic reagents or nucleophilic reagents added in excess and remaining unreacted in the reaction liquid, and compounds having electrophilicity and nucleophilicity produced as byproducts in the chemical reaction. Alternatively, in the case of using the reagent for organic synthesis of the present embodiment as a nucleophilic scavenger, and an electrophilic scavenger, it is also possible to bond it to the unreacted reaction substrate, and make the reaction proceed on the reagent for organic synthesis. The reagent for organic synthesis which can be used in such reactions is not particularly limited, and for example, in the reagent for organic synthesis shown in Chemical Formula (1), a reagent for organic synthesis wherein the reagent active site X is shown by (A) to (C) or (A') to (C') if a nucleophilic scavenger, or the reagent active site X is shown by (D) to (H) and (M), or (D') to (H') and (M') if an electrophilic scavenger, can be mentioned.

The added amount of the reagent for organic synthesis used in the reaction can be appropriately set by one skilled in the art in consideration of the solubility of the reagent for organic synthesis with respect to the used solvent, and the electrophilicity and nucleophilicity of the compound to be captured and the like, and it is preferable to add from 1 to 5 equivalents of the reagent for organic synthesis with respect to one equivalent of the expected residual amount of the nucleophilic or electrophilic reaction substrate.

For the case of using the reagent for organic synthesis of the present embodiment as a nucleophilic scavenger, for example, a form of use such as the following can be mentioned.

Namely, in the case of carrying out a peptide synthesis reaction using an active amino acid in an N,N-dimethylformamide/propionitrile mixed solvent, a peptide bond is formed when adding an excess amount of the activated amino acid with respect to the N terminal amino group of the peptide. Because the excess active amino acid remaining in the reaction system has electrophilicity, it is easy to form an ester bond with this by adding the compound shown in Chemical Formula (2). After the reaction, by adding a solvent such as cyclohexane or the like, it is possible to recover the nucleophilic scavenger bonded to the active amino acid from the amide layer, and a peptide to which 1 amino acid residue is attached, at the N terminal of the peptide before the reaction, remains in the reaction system.

Use of the Reagent for Organic Synthesis as a Peptide Synthesis Reagent

Among the reagents for organic synthesis of the present embodiment, those shown by Chemical Formula (1) where X indicates (M) or (M') can be used as electrophilic scavengers, and especially, can be used as peptide synthesis reagents. In the case of use as a peptide synthesis reagent, in the reagent active site shown by Chemical Formulas (M) and (M'), a carbon atom bonded to the hydroxyl group in the reagent active site, as well as a carbon atom bonded to the halogen atom which is not directly bonded to the benzene ring, have electrophilicity, and thus can bond with the carboxyl group of the amino acid, and thus the peptide synthesis reaction can be carried out by sequentially forming bonds to an activated amino acid in the state wherein the carboxyl group is bonded to the reagent for organic synthesis.

At the completion of the peptide synthesis reaction, by adding acid to the reagent for organic synthesis separated from the reaction system, it is possible to easily separate only the peptide. Here, the reagent for organic synthesis having a reagent active site (M) or (M') does not activate the carbonyl group when the amino acid is bonded to the reagent for organic synthesis, and thus there is no generation of intermediates having an oxazolone skeleton which would lead to racimization of the $\alpha$ carbon, and thus in the process of peptide synthesis, racimization of the peptide does not occur.

Further, applications of the reagent for organic synthesis having a reagent active site (M) or (M') are not limited to applications as a reagent for peptide synthesis. Specifically, for example, applications as a hydrophobic carrier group, by reacting the reagent for organic synthesis having a reagent active site with the desired compound, can be mentioned. Such reagents for organic synthesis used as a hydrophobic carrier group are also included within the scope of the present invention.

Use of the Reagent for Organic Synthesis as a Metal Ligand

By using the reagent for organic synthesis as a metal ligand, the reagent for organic synthesis can coordinate with and capture metal ions added to the reaction system as catalysts or the like. The reagent for organic synthesis which can be used for such a reaction is not particularly limited, and for example, in the reagent for organic synthesis shown by Chemical Formula (1), a reagent for organic synthesis where X is a reagent active site shown by (K) or (K') can be mentioned.

The added amount of the reagent for organic synthesis used in the reaction can be appropriately set by one skilled in the art in consideration of the solubility of the reagent for organic synthesis with respect to the solvent, and the normal coordination number of the metal ion and the like, and it is preferable to add from 1 to 5 equivalents of the reagent for organic synthesis with respect to one equivalent of the added metal ion.

For the case of using the reagent for organic synthesis as a nucleophilic scavenger, electrophilic scavenger, or metal ion ligand, in the chemical reaction preceding the reaction for trapping the excess compounds and the like, it is possible to use a solvent commonly used in this reaction, and in the present embodiment, from the point of the solubility of the reagent for organic synthesis having a hydrophobic carrier group, it is preferable to use tetrahydrofuran, dichloromethane, a cyclohexane/N,N-dimethylformamide mixed solvent or the like as the solvent.

Separation Step

The reagent for organic synthesis of the present embodiment reacts sharply to changes in the solution composition and/or temperature, and crystallizes. Because of this, it is possible to crystallize the reagent for organic synthesis using the means of changing the composition and/or temperature of the solution. Further, the separation step of the reagent for organic synthesis can by carried out by liquid liquid extraction separation, by adding a separation solvent which is immiscible with the reaction solvent used in the reaction step, but which can easily dissolve the reagent for organic synthesis.

Separation by Changing the Solution Composition

As a preferred means for changing the solution composition, for example, the means of adding a poor solvent for the reagent for organic synthesis to the reaction solution can be mentioned. Here, by adding a solvent with high affinity for the reaction solvent, there is no phase separation of the liquid phase, and thus is it possible to easily change the solution composition. As the poor solvent, it is possible to use any solvent, and it is possible to use the same solvent used as the reaction solvent, and a solvent which differs form the reaction solvent. For example, in the case of using dichloromethane, tetrahydrofuran and diethylether or the like as the reaction solvent, it is possible to use acetonitrile, N,N-dimethylformamide, and methanol and the like as the poor solvent. By adding the poor solvent to the reaction solvent, the polarity of the solution increases, and the reagent for organic synthesis, and the reacted reagent for organic synthesis can crystallize and solid liquid separation becomes possible. When carrying out the solid liquid separation, it is possible to use a suction filter such as, for example, a separatory funnel, and in order to complete the separation of the products from a reagent having a hydrophobic carrier group, an octadecylsilylated (ODS) silica gel filter or an ODS short column may be used.

Separation by Concentration of the Solution

As another preferable means for changing the solution composition, for example, the means of concentrating the solvent of the solution in which the reagent for organic synthesis, and the reacted reagent for organic synthesis are dissolved, can be mentioned. Here, concentrating refers to distilling away a part of the solvent. When distilling a part of the solvent, it is preferable to carry out the distillation within a range wherein the reagent for organic synthesis, and the reacted reagent for organic synthesis crystallize, while the synthesized desired compound does not crystallize. These conditions can be appropriately set by one skilled in the art in consideration of the added amount of the reagent for organic synthesis, the estimated produced amount of the desired compound, the solubility of each compound and the like.

Separation by Changing the Solution Temperature

In the separation step, by changing the solution temperature, it is possible to crystallize and separate the reagent for organic synthesis and the reacted reagent for organic synthesis. In the present embodiment, as a preferably used means for changing the solution temperature, there is no particular limitation so long as it is a means for changing the temperature of the solution in which the reagent for organic synthesis and the reacted reagent for organic synthesis are dissolved. Specifically, the means of cooling the solution can be mentioned. For example, in the case of using cyclohexane as the reaction solvent, by cooling to 5° C. or less, it is possible to crystallize the reagent for organic synthesis and the reacted reagent for organic synthesis. Further, in the case of using N,N-dimethylformamide as the reaction solvent, by heating in the reaction step, the solubility of the reagent for organic synthesis increases, and by cooling after the reaction, the reagent for organic synthesis and the reacted reagent for organic synthesis can be crystallized.

In the case of crystallizing the reagent for organic synthesis by changing the solution composition and the solution temperature, by adding octadecylsilylated silica gel, glass beads or the like as crystallization seeds, it is possible to easily form the crystals.

Separation by Liquid Liquid Extraction

In the separation step, by adding a separation solvent which does not mix with the reaction solvent in which the reagent for organic synthesis is dissolved in the reaction step, and for which the solubility of the reagent for organic synthesis is greater than the solubility of the reagent for organic synthesis in the reaction solvent, it is possible to dissolve the reagent for organic synthesis and the reacted reagent for organic synthesis in the separation solvent. By separating with a separatory funnel the separation solvent in which the reagent for organic synthesis, and the reacted reagent for organic synthesis are dissolved, it is possible to easily separate the reagent for organic synthesis, and the reacted reagent for organic synthesis from the reaction solvent.

In the present embodiment, the separation solvent which can be used is not particularly limited, and in the case of using acetonitrile, propionitrile, and N,N-dimethylformamide or the like as a reaction solvent, for example, cyclohexane, and decalin or the like can be used.

Namely, for example, in the case of using N,N-dimethylformamide as the reaction solvent, by adding cyclohexane as the separation solvent to the reaction system after the completion of the chemical reaction, heating, and then cooling, the reagent for organic synthesis, and the reacted reagent for organic synthesis are selectively distributed into the cyclohexane phase. By separating the cyclohexane phase with a separatory funnel, it is possible to obtain an N,N-dimethylformamide solution from which the reagent for organic synthesis, and the reacted reagent for organic synthesis have been removed.

In the method of organic synthesis reaction of the present embodiment, after separating the reagent for organic synthesis, it is possible to further carry out a process for separating the reagent for organic synthesis and an atomic group bonded to the reaction active site, and to isolate the separated atomic group. In such a case, as a reagent which can be used when separating the reagent for organic synthesis and the atomic group bonded to the reaction active site, trifluoroacetate, and acids such as hydrochloric acid and the like; bases such as sodium hydroxide; as well as hydrogenation catalysts such as palladium and the like can be mentioned. Among these, trifluoroacetate can be preferably used.

EXAMPLES

The present invention is explained below with reference to the following Examples, but the present invention is not in any way limited by these examples.

Example 1

Synthesis of an Amine Having a Hydrophobic Carrier Group

One gram of 2,4-dihydroxybenzaldehyde, 8.4 g of 1-bromodocosane, and 6 g of potassium carbonate were dissolved in 20 ml of N,N-dimethylformamide, and reacted for 8 hours under a nitrogen gas flow at 80° C. After confirming the completion of the reaction by thin layer chromatography, 20 ml of toluene and 10 ml of water were added to the reaction liquid and stirred for 5 min at 80° C. The toluene layer was separated with a separatory funnel and after removal by distillation of the solvent, 50 ml of methanol were added and crystals were precipitated. This solution was subjected to suction filtration with a separatory funnel and 6.97 g of crude crystals w ere obtained. After dissolving the crude crystals in 200 ml of hexane at 70° C. and recrystallizing at room temperature, suction filtration was again carried out with a separatory funnel, and 4.7 g of the desired compound 3 were obtained. The yield was 85%. Compound 3; 2,4-bis(docosyloxy)benzaldehyde.

Then, 1.9 g of compound 3 were set aside and dissolved in dichloromethane, and 500 mg of hydroxyamine hydrochloride, and an excess amount of triethylamine were added and reacted for 6 hours at room temperature. After the completion of the reaction, the solution was concentrated, and 50 ml of acetonitrile were added and the product was crystallized. This solution was suction filtered with a separatory funnel and 1.9 g of compound 4 were obtained. The yield was 98%. Compound 4; 2,4-bis(docosyloxy)benzaldehyde oxime.

Next, 770 mg of compound 4 were set aside and dissolved in tetrahydrofuran, 150 mg of lithium aluminum hydride were added at room temperature and stirred, and after this, heating and refluxing were carried out. After the completion of the reaction was confirmed by thin layer chromatography, 5 ml of methanol and 50 ml of toluene were added and the organic layer was washed with an aqueous solution of 1 N hydrochloric acid, neutralized with a saturated sodium hydrogen carbonate solution, and washed with a saturated saline solution. The organic layer was separated and vacuum distillation removed, and after this, 50 ml of methanol were added and crystals precipitated. This solution was suction filtered with a separatory funnel and 719 mg of compound 5 were obtained. The yield was 95%. Compound 5; (2,4-bis(docosyloxy)phenyl)methane amine.

The above reactions are shown below.

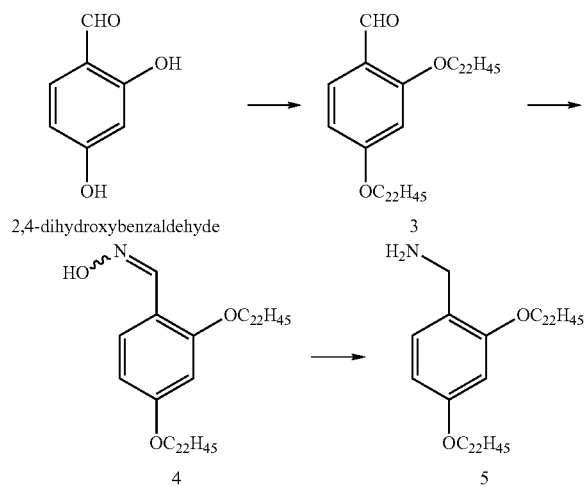

Structural Analysis of Compound 3
$^1$H-NMR (CDCl$_3$, 300 MHz) δ 10.32 (1H, s), 7.78 (1H, d, J=8.62 Hz), 6.50 (1H, dd J=8.62, 2.20 Hz), 6.41 (1H, d, J=2.20 Hz), 4.04 (1H, d, J=6.60 Hz), 3.99 (1H, d, J=6.60 Hz), 1.81 (4H, m), 1.51-1.18 (76H, m), 0.88 (6H, t, J=6.60 Hz)

Structural Analysis of Compound 4
$^1$H-NMR (CDCl$_3$, 300 MHz) δ 8.45 (1H, s), 7.65 (1H, d, J=8.40 Hz), 6.46 (1H, dd J=8.40, 2.20 Hz), 3.96 (2H, t, J=6.42 Hz), 3.95 (2H, t, J=6.42 Hz), 1.78 (4H, m), 1.50-1.15 (76H, m), 0.88 (6H, t, J=6.80 Hz)

Structural Analysis of Compound 5
$^1$H-NMR (CDCl$_3$, 300 MHz) δ 8.45 (1H, s), 7.65 (1H, d, J=8.40 Hz), 6.46 (1H, dd J=8.40, 2.20 Hz), 3.96 (2H, t, J=6.42 Hz), 3.95 (2H, t, J=6.42 Hz), 1.78 (4H, m), 1.50-1.15 (76H, m), 0.88 (6H, t, J=6.80 Hz)

Example 2

Synthesis of an Isocyanate Having a Hydrophobic Carrier Group

An amount of 371 mg (0.4 mmol) of 3,4,5-tris(octadecyloxy)benzoic acid was dissolved in 5 ml of toluene, and mixed with 412 mg (1.50 mmol) of diphenylphosphoryl azide (DPPA) and 30 mg (0.4 mmol) of triethylamine. This was stirred for 3 hours at room temperature, and then, heated to 90° C., and further reacted for 3.5 hours. After the completion of the reaction, acetonitrile was added, and after the precipitation of crystals, suction filtration was carried out with a separatory funnel and 333 mg of compound 6 were obtained. The yield was 90%. Compound 6; 5-isocyanate-1,2,3-tris(octadecyloxy)benzene.

The above reactions are shown below.

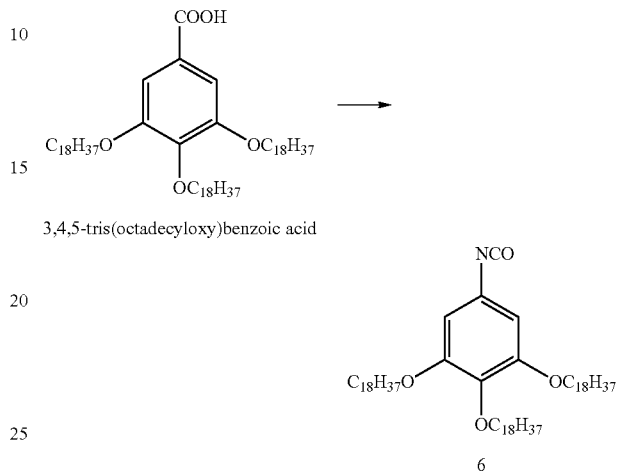

Structural Analysis of Compound 6
$^1$H-NMR (CDCl$_3$, 400 MHz) δ 6.20 (2H, s), 3.98-3.92 (6H, m), 1.82-1.69 (6H, m), 1.49-1.23 (84H, m), 0.88 (9H, t, J=6.60 Hz)

Example 3

Synthesis of a Chloroformate Having a Hydrophobic Carrier Group

An amount of 4.43 g of methyl 3,5-bis(docosyloxy)benzoate was dissolved in 100 ml of tetrahydrofuran, and 240 mg of lithium aluminum hydride were introduced and stirred at room temperature. After the completion of the reaction was confirmed by thin layer chromatography, 1 ml of methanol was added and the reaction was stopped. After this, 30 ml of 1 N hydrochloric acid was added, and the extracted organic layer was washed two times with 30 ml of 1 N hydrochloric acid, once with 30 ml of a saturated aqueous solution of sodium hydrogen carbonate, and twice with 30 ml of saturated saline solution, and dried with magnesium sulfate. After vacuum distillation of the solution, 100 ml of methanol were added and crystals precipitated, and suction filtration was carried out using a separatory funnel to obtain 3.62 g of compound 7. The yield was 80%. Compound 7; 3,5-bis(docosyloxy)benzyl alcohol An amount of 5 g of compound 7 was dissolved in 50 ml of toluene, 4.86 g of triphosgene were added, and reacted for 2 hours under a nitrogen gas flow at room temperature. After this, the reaction liquid was heated to 40° C., and further stirred for 1 hour. After the completion of the reaction was confirmed by thin layer chromatography, drying was carried out for 2 hours at 3 mmHg under a vacuum pump at 40° C. to obtain 5.1 g of compound 8. The yield was 94%. Compound 8; 3,5-bis(docosyloxy)benzylcarbonochloridate The above reactions are shown below.

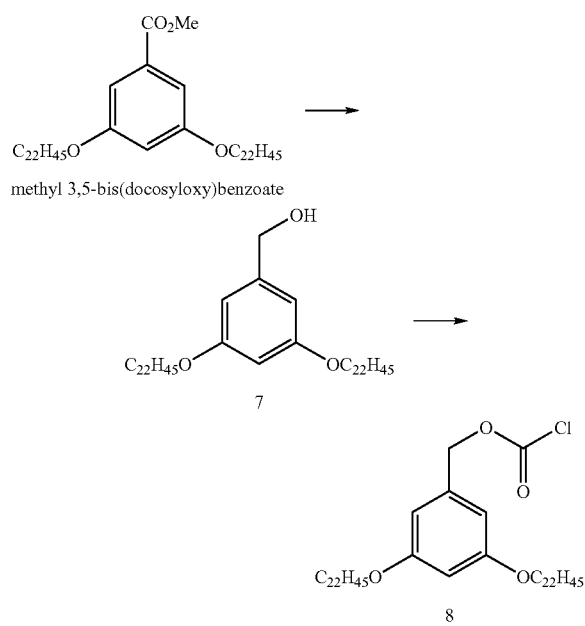

methyl 3,5-bis(docosyloxy)benzoate

Structural Analysis of Compound 7
$^1$H-NMR (CDCl$_3$, 300 MHz) δ 6.49 (2H, d, J=2.20 Hz), 6.37 (1H, t, J=2.20 Hz), 4.60 (2H, s), 3.92 (4H, t, J=6.60 Hz), 1.76 (4H, m), 1.49-1.18 (76H, m), 0.88 (6H, t, J=6.60 Hz)

Structural Analysis of Compound 8
$^1$H-NMR (CDCl$_3$, 300 MHz) δ 6.49 (2H, d, J=2.20 Hz), 6.45 (1H, t, J=2.20 Hz), 5.20 (2H, s), 3.93 (4H, t, J=6.79 Hz), 1.76 (4H, m), 1.52-1.13 (76H, m), 0.88 (6H, t, J=6.60 Hz)

Example 4

Synthesis of a Carbamate Having a Hydrophobic Carrier Group

An amount of 756 mg (1.0 mmol) of the compound 7 synthesized in Example 3 was set aside, and dissolved in 20 ml of dichloromethane. Then, 810 mg (5.0 mmol) of 1,1'-carbonyldiimidazole was added, and stirred for 4 hours at room temperature. After the completion of the reaction was confirmed by thin layer chromatography, the solvent was distilled under a vacuum, acetonitrile was added, and crystallization occurred. This was suction filtered using a separatory funnel, and 850 mg of compound 9 were obtained. The yield was 99%. Compound 9; 3,5-bis(docosyloxy)benzyl 1H-imidazole-1-carboxylate The above reactions are shown below.

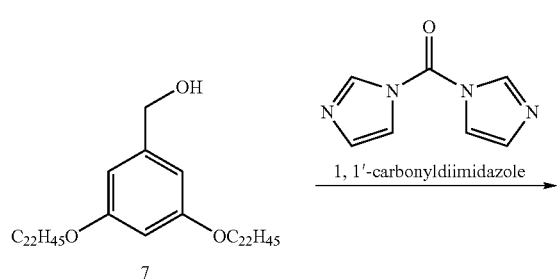

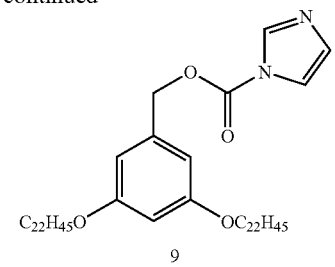

Structural Analysis of Compound 9
$^1$H-NMR (CDCl$_3$, 400 MHz) δ 8.15 (1H, m), 7.44 (1H, m), 7.06 (1H, m), 6.53 (2H, d, J=2.21 Hz), 6.46 (1H, t, J=2.21 Hz), 5.32 (2H, s), 3.93 (4H, t, J=6.42 Hz), 1.75 (4H, m), 1.49-1.16 (76H, m), 0.88 (6H, t, J=6.97 Hz)

Example 5

Synthesis of a Bromine Compound Having a Hydrophobic Carrier Group

To a dried recovery flask, 915.0 mg (1 mmol) of 3,4,5-trisoctadecyloxybenzyl alcohol were added, and dissolved in 10 ml of dichloromethane. Then, 406.3 mg (1.5 mmol) of phosphorus tribromide were added, and stirred for 3 hours at room temperature. After confirming the completion of the reaction by thin layer chromatography, 1 ml of water was added and the reagent was deactivated. After this, liquid liquid extraction was carried out with hexane, and then washing was carried out with a saturated saline solution, and an organic phase was obtained. The solvent was distilled under a vacuum from this organic phase, and suction filtration was carried out using a separatory funnel, and 988.1 g of compound 10 were obtained. The yield was 99%. Compound 10; 3,4,5-trisoctadecyloxybenzylbromide The above reactions are shown below.

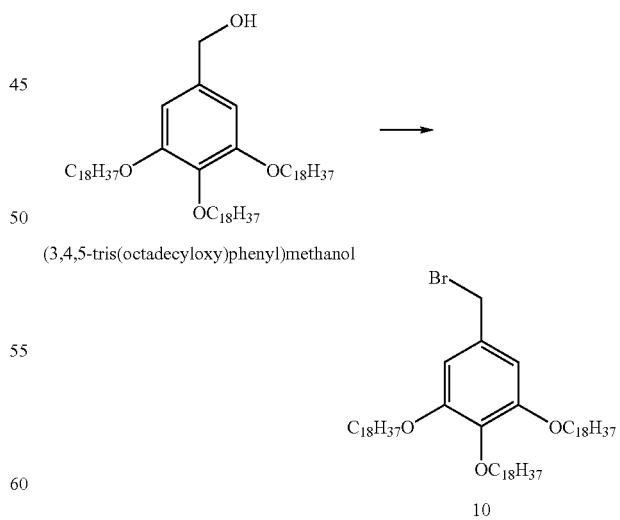

Structural Analysis of Compound 10
$^1$H-NMR (CDCl$_3$, 400 MHz) δ 6.57 (2H, s), 4.43 (2H, s), 3.98-3.92 (6H, m), 1.82-1.69 (6H, m), 1.50-1.42 (6H, m), 1.33-1.23 (84H, m), 0.88 (9H, t, J=7.0 Hz)

Infrared Absorption Spectrum (KBr) δδ2954, 2920, 2848, 1591, 1504, 1466, 1441, 1394, 1246, 1213, 1115 (units: cm$^{-1}$)

Example 6

Synthesis of a Basic Compound Having a Hydrophobic Carrier Group

Into a dried recovery flask 1.46 g (1.5 mmol) of compound 10 synthesized in Example 5 were set aside and dissolved in 20 ml of N,N-dimethylformamide. Then, 443.1 mg (2 equivalents) of potassium carbonate, 369.4 mg (1 equivalent) of tetrabutylammonium iodide, and 1.05 g (5 equivalents) of 1,5,7-triazabicyclo[4,4,0]deca-5-ene were added, and stirred for 4 hours at 80° C. After the completion of the reaction was confirmed by thin layer chromatography, liquid liquid extractions were carried out with hexane, and then with a saturated saline solution, and an organic phase was obtained. This organic phase was distilled under a vacuum, methanol was added and crystallization occurred, and then suction filtration was carried out with a separatory funnel, and 1.3 g of compound II were obtained. The yield was 84%. Compound 11; 1-(3,4,5-tris(octadecyloxy)benzyl)-2,3,4,6,7,8-hexahydro-1H-pyrimido[1,2-a]pyrimidine.

The above reactions are shown below.

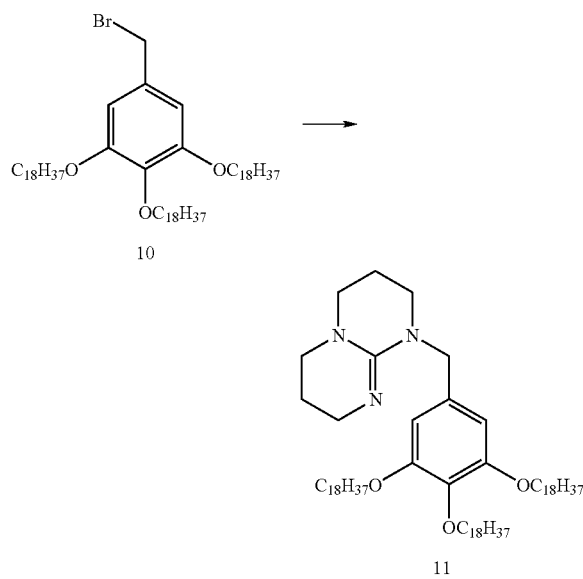

Structural Analysis of Compound 11

$^1$H-NMR (CDCl$_3$, 600 MHz) δ 6.46 (2H, s), 4.49 (2H, s), 3.94 (4H, t, J=6.6), 3.91 (2H, t, J=6.6), 3.41 (2H, t, J=5.5), 3.18 (2H, t, J=5.9), 3.13 (2H, t, J=5.9), 3.03 (2H, t, J=5.9), 1.89 (4H, m), 1.79-1.70 (6H, m), 1.48-1.43 (6H, m), 1.35-1.21 (84H, m), 0.87 (9H, t, J=7)

Infrared Absorption Spectrum (KBr): 2954, 2916, 2850, 1593, 1504, 1468, 1435, 1381, 1228, 1115, 835 (units: cm$^{-1}$)

Example 7

Synthesis of a Triphenylphosphine Having a Hydrophobic Carrier Group

An amount of 756 mg (1.0 mmol) of the compound 7 synthesized in Example 3 was set aside and dissolved in 20 ml of dichloromethane. Then, 612 mg (2.0 mmol) of 4-(diphenylphosphino) benzoic acid, 25 mg (0.2 mmol) of dimethylaminopyridine, 631 mg (5.0 mol) of dicyclohexylcarbodiimide were added, and stirred for 4 hours at room temperature. After the completion of the reaction was confirmed by thin layer chromatography, the solvent was distilled under a vacuum, and acetonitrile was added and crystallization occurred, and suction filtration was carried out using a separatory funnel, and 1.0 g of compound 12 were obtained. The yield was 96%. Compound 12; 3,5-bis(docosyloxy)benzyl-4-(diphenylphosphino)benzoic acid The above reactions are shown below.

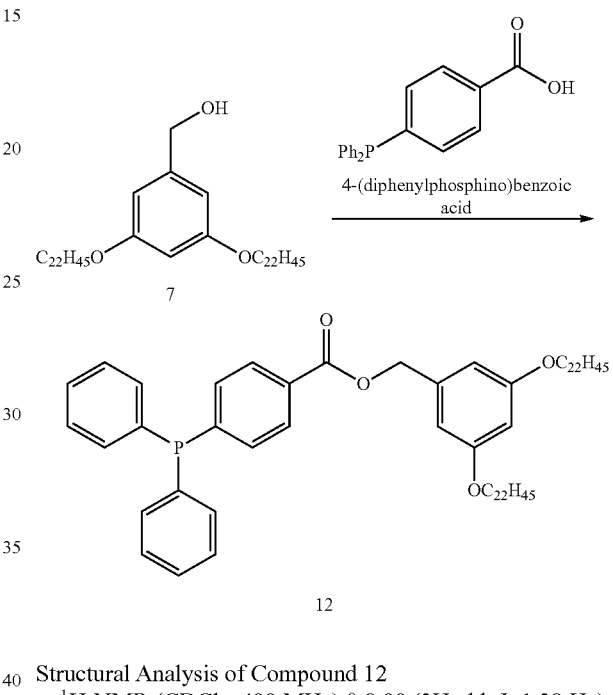

Structural Analysis of Compound 12

$^1$H-NMR (CDCl$_3$, 400 MHz) δ 8.00 (2H, dd, J=1.28 Hz), 7.39-7.27 (12H, m), 6.53 (2H, d, J=2.01 Hz), 6.41 (1H, t, J=2.01 Hz), 5.26 (2H, s), 3.92 (4H, m), 1.75 (4H, m), 1.49-1.14 (76H, m), 0.88 (6H, t, J=6.97 Hz)

Example 8

Synthesis of an Azodicarboxylate Ester Having a Hydrophobic Carrier Group

An amount of 850 mg (1.0 mmol) of the compound 9 synthesized in Example 4 was set aside, and dissolved in 10 ml of toluene. Then, 312 mg (3.0 mmol) of ethyl carbazate, and 303 mg (3.0 mmol) of triethylamine were added, and stirred for 18 hours at 120° C. After completion of the reaction, the solvent was distilled, and 100 ml of acetonitrile were added, and the precipitated crystals were suction filtered, and 798 mg of compound 13 were obtained. The yield was 90%. Next, 888 mg of compound 13 (1.0 mmol) were set aside and after dissolving in 10 ml of dichloromethane, 644 mg (2.0 mmol) of iodobenzene acetate were added, and stirred for 3 hours at room temperature. After confirming the completion of the reaction by thin layer chromatography, the solvent was distilled under a vacuum, and 10 ml of acetonitrile were added and crystallization occurred. Suction filtration was carried out using a separatory funnel and the crystals were separated, and 620 mg of compound 14 were obtained. The yield was 70%.

Compound 13; 1-(3,5-bis(docosyloxy)benzyl)-2-ethylhydrazine-1,2-dicarboxylate. Compound 14; 1-(3,5-bis(docosyloxy)benzyl)-2-ethyldiazine-1,2-dicarboxylate.

The above reactions are shown below.

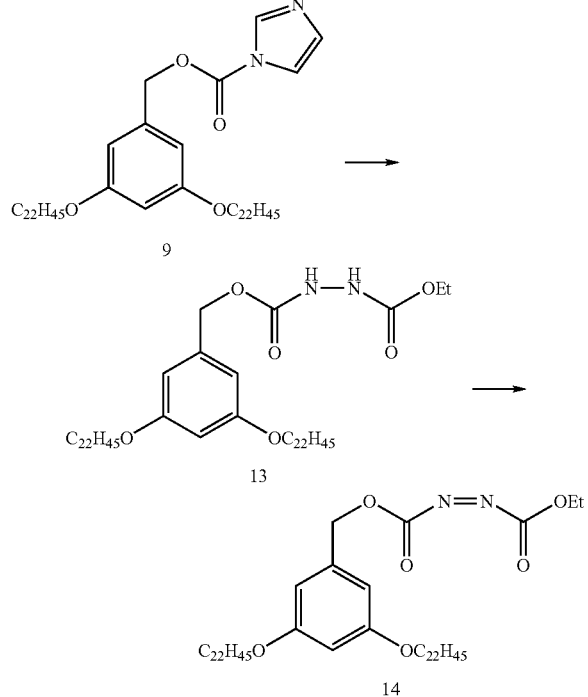

Structural Analysis of Compound 13

$^1$H-NMR (CDCl$_3$, 400 MHz) δ 6.45 (2H, d, J=2.20 Hz), 6.37 (1H, t, J=2.20 Hz), 5.07 (2H, s), 4.19 (2H, q, J=7.34 Hz), 3.89 (4H, t, J=6.60 Hz), 1.73 (4H, m), 1.46-1.14 (76H, m), 0.86 (6H, t, J=6.60 Hz)

Structural Analysis of Compound 14

$^1$H-NMR (CDCl$_3$, 400 MHz) δ 6.52 (2H, d, J=2.20 Hz), 6.39 (1H, t, J=2.20 Hz), 5.32 (2H, s), 4.49 (2H, m), 3.89 (4H, m), 1.73 (4H, m), 1.46-1.14 (76H, m), 0.86 (6H, t, J=6.60 Hz)

Example 9

Scavenging of 4-Chlorobenzylamine Using an Isocyanate Having a Hydrophobic Carrier Group Amounts of 141 mg (1.0 mmol) of 4-chlorobenzylamine and 183 mg (1.0 mmol) of N-(4-chlorobenzyl)acetamide were dissolved in 20 ml of dichloromethane. To the solution, 1.0 g (1.1 mmol) of the compound 6 synthesized in Example 2 were added, and after stirring for 10 minutes, 50 ml of acetonitrile were added. After distilling the dichloromethane under a vacuum at room temperature, the crystals were filtered with a separatory funnel. On distilling the filtrate, N-(4-chlorobenzyl)acetamide was quantitatively recovered, and the crystals were compound 15. Compound 15; 1-(4-chlorobenzyl)-3-(3,4,5-tris(octadecyloxy)phenyl)urea The above reactions are shown below.

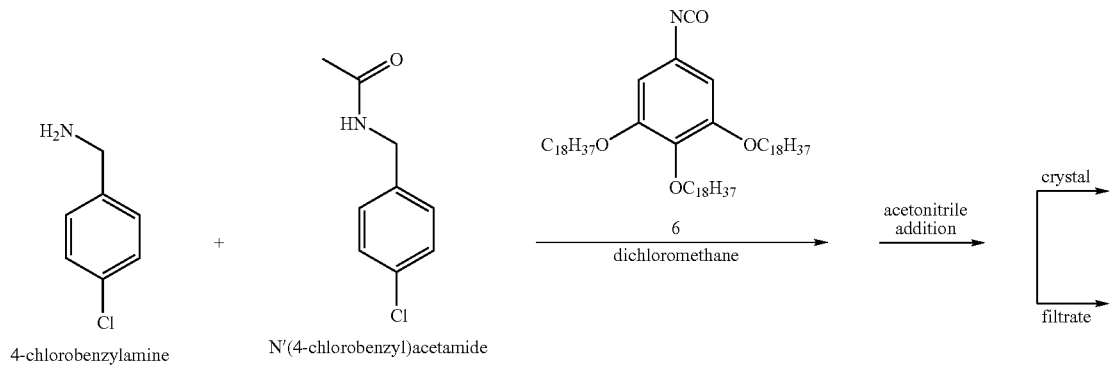

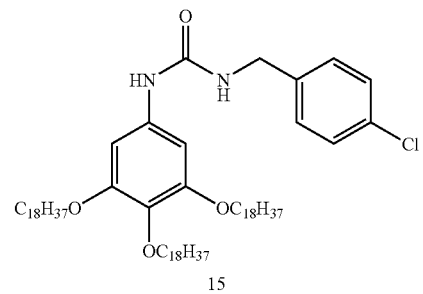

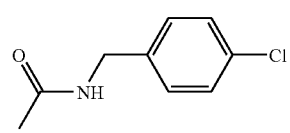

Structural Analysis of Compound 15

¹H-NMR (CDCl₃, 300 MHz) δ 7.10 (4H, m), 6.45 (2H, s), 6.39 (2H, m), 3.90 (6H, m), 1.77 (6H, m), 1.53-1.17 (90H, m), 0.86 (6H, t, J=6.60 Hz)

Example 10

Synthesis Reaction of Diketopiperazine Using a Base Having a Hydrophobic Carrier Group An amount of 278 mg (0.2 mmol) of 3,4,5-tris(octadecyloxy)benzyl-1-(2-(((9H-fluoren-9-yl)methoxy)carbonylamino)-3-phenylpropanoyl)pyrrolidine-2-carboxylate were dissolved in 20 ml of dichloromethane. To this, 205 mg (0.2 mmol) of the compound 11 synthesized in Example 6 were added, and stirred for 7 hours. After the reaction, 50 ml of acetonitrile were added. After distilling the dichloromethane under a vacuum at room temperature, the crystals were filtered with a separatory funnel. The filtrate was vacuum distilled, and 35.1 mg of diketopiperazine were obtained. The yield was 72%.

Comparative Example 1

Synthesis Reaction of Diketopiperazine Using a Base Carried on a Polystyrene

An amount of 278 mg (0.2 mmol) of 3,4,5-tris(octadecyloxy)benzyl-1-(2-((9H-fluorene-9-yl)methoxy)carbonylamino)-3-phenylpropanoyl)pyrrolidine-2-carboxylate were dissolved in 20 ml of dichloromethane. To this, 600 mg (amino group equivalent 1.2 mmol) of "TBD-methyl polystyrene" (manufactured by Novabiochem) was added and stirred for 21 hours. The reaction liquid was filtered, and after distilling the solvent, 50 ml of acetonitrile were added. After filtering the crystals in a separatory funnel, the filtrate was vacuum distilled, and 18.5 mg of diketopiperazine were obtained. The yield was 38%.

Comparative Example 2

Synthesis Reaction of Diketopiperazine Using a Base Carried on a Silica Gel

An amount of 278 mg (0.2 mmol) of 3,4,5-tris(octadecyloxy)benzyl-1-(2-(((9H-fluorene-9-yl)methoxy)carbonylamino)-3-phenylpropanoyl)pyrrolidine-2-carboxylate was dissolved in 20 ml of dichloromethane. To this, 1200 mg (amino group equivalent 1.2 mmol) of "Si-TBD" (manufactured by Sigma Aldrich) was added and stirred for 21 hours. The reaction liquid was filtered, and after the distillation of the solvent, 50 ml of acetonitrile were added. After filtration of the crystals with a separatory funnel, the filtrate was vacuum distilled, and 7.3 mg of diketopiperazine were obtained. The yield was 15%.

The reactions of Example 10, and Comparative Examples 1 and 2 are shown below.

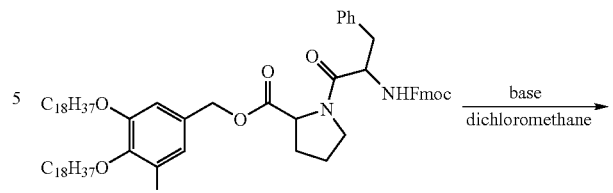

3,4,5-tris(octadecyloxy)benzyl-(2-(((9H-fluoren-9-yl)methoxy)carbonylamino)-3-phenylpropanoyl)pyrrolidine-2-carboxylate

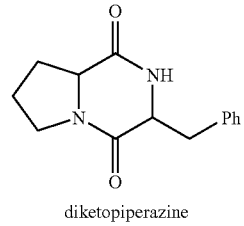

diketopiperazine

A comparison of the yields of Example 10, and Comparative Examples 1 and 2 is shown in Table 1.

TABLE 1

|  | Example 10 | Comparative Example 1 | Comparative Example 2 |
|---|---|---|---|
| Amount of Base (Equivalent) | 1 | 6 | 6 |
| Reaction Time (hr) | 7 | 21 | 21 |
| Yield (%) | 72 | 38 | 15 |

Example 11

Mitsunobu Reaction Using an Azodicarboxylate Ester Having a Hydrophobic Carrier Group Into an recovery flask, 16 mg (0.1 mmol) of 2-(4-methoxyphenyl)acetic acid, and 7 mg (0.1 mmol) of isopropanol were added, and dissolved in 5 ml of tetrahydrofuran. To this, 52 mg (0.2 mmol) of triphenylphosphine, and 177 mg (0.2 mmol) of the compound 14 of Example 8 were added, and stirred for 24 hours at room temperature. The solvent was distilled under a vacuum, acetonitrile was added, and filtration was carried out with an octadecylsilyl silica packed syringe, and from the filtrate, 16.7 mg of isopropyl-2-(4-methoxyphenyl)acetate was obtained. The yield was 70%.

The above reactions are shown below.

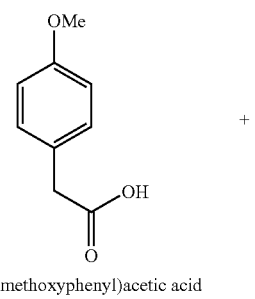

2-(4-methoxyphenyl)acetic acid

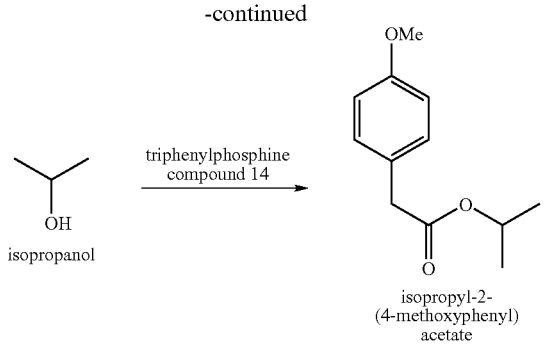

Example 12

Peptide Synthesis Reaction

An amount of 785 mg (1.0 mmol) of methyl 3,5-bis(docosyloxy)benzoate was dissolved in 20 ml of tetrahydrofuran, and 18 ml (9 equivalents) of 4-chlorophenylmagnesiumbromide tetrahydrofuran solution was added, and stirring was carried out for 2 hours at 76° C. After confirming the completion of the reaction by thin layer chromatography, 30 ml of 1 N hydrochloric acid was added and the reaction was stopped. After this, extraction was carried out 3 times with 30 ml of hexane, and the obtained organic phase was further washed one time with 30 ml of 1 N hydrochloric acid, one time with saturated sodium hydrogen carbonate, and one time with saturated saline solution, and dried with magnesium sulfate. After vacuum distillation of the solvent, 100 ml of methanol was added and crystals were precipitated, and suction filtration was carried out with a separatory funnel to obtain 780 mg of compound 16. The yield was 80%. Compound 16; 3,5-bis(docosyloxy)phenyl-4,4-dichlorophenyl alcohol.

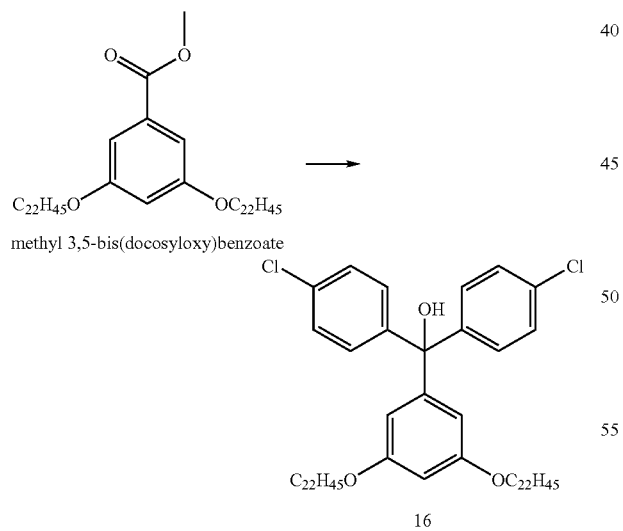

Structural Analysis of Compound 16

$^1$H-NMR (CDCl$_3$, 400 MHz) δ 7.30-7.26 (4H, m), 7.23-7.17 (4H, m), 6.44-6.32 (2H, m), 6.32-6.30 (1H, m), 3.84 (4H, t, J=6.6 Hz), 1.67-1.63 (4H, m), 1.27-1.24 (76H, m), 0.88 (6H, t, J=7.0 Hz)

An amount of 294 mg (0.3 mmol) of compound 16 were dissolved in 5 ml of dichloromethane, and 1 ml of acetyl chloride was added and reacted for 1 hour at 45° C. After confirming the completion of the reaction by thin layer chromatography, vacuum distillation was carried out and the solvent was distilled, and a crystalline substance (compound 17) was obtained. The thus obtained crystals were dissolved in 10 ml of dichloromethane, and 180 mg (1.5 equivalents) of Fmoc-Cys(tBu)-OH, and 262 μl (5 equivalents) of diisopropylethylamine were added and reacted for 30 min at 0° C. After confirming the completion of the reaction by thin layer chromatography, 500 μl of diazabicycloundecene were added, and further reacted for 10 minutes. After again confirming the completion of the reaction by thin layer chromatography, 100 ml of acetonitrile was added, and the solution was gradually vacuum filtered and crystals were precipitated, and suction filtration was carried out using a separatory funnel and a crystalline substance was obtained.

The thus obtained crystalline substance was dissolved in 10 ml of dichloromethane, and 175 mg (1.5 equivalents) of Fmoc-Phe-OH, 188 μl (4 equivalents) of diisopropylcarbodiimide, and 162 mg (4 equivalents) of 1-hydroxybenzotriazole were added and reacted for 1 hr at room temperature. After confirming the completion of the reaction by thin layer chromatography, 100 ml of acetonitrile were added, and the solvent was gradually vacuum distilled and crystals were precipitated, and suction filtration was carried out using a separatory funnel and 371 mg of compound 18 were obtained. The yield was 83%. The thus obtained crystalline substance was dissolved in 10 ml of a previously adjusted 0.1% trifluoroacetic acid/dichloromethane solution and reacted for 1 hour. After confirming the completion of the reaction by thin layer chromatography, 100 ml of acetonitrile were added, and the solution was gradually vacuum distilled and crystals were precipitated, and suction filtration was carried out using a separatory funnel. By vacuum distillation of the obtained solution, the desired compound Fmoc-Phe-Cys(tBu)-OH (compound 19) was obtained. Further, confirmation of the desired product was carried out in a mass spectrograph. Compound 17; chloro-3,5-bis(docosyloxy)phenyl-4,4-dichlorophnylmethane

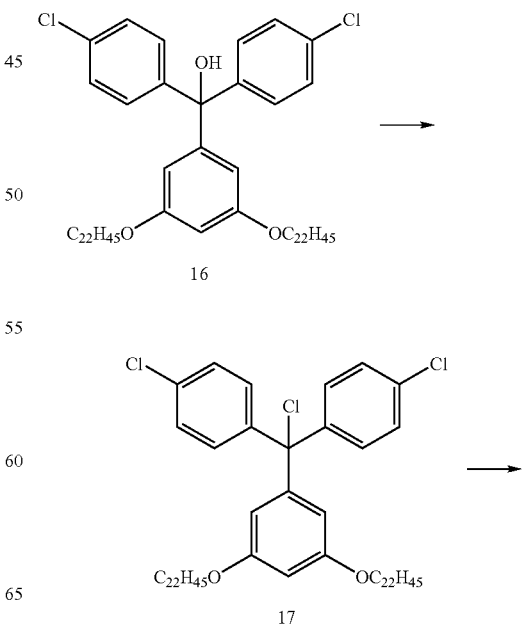

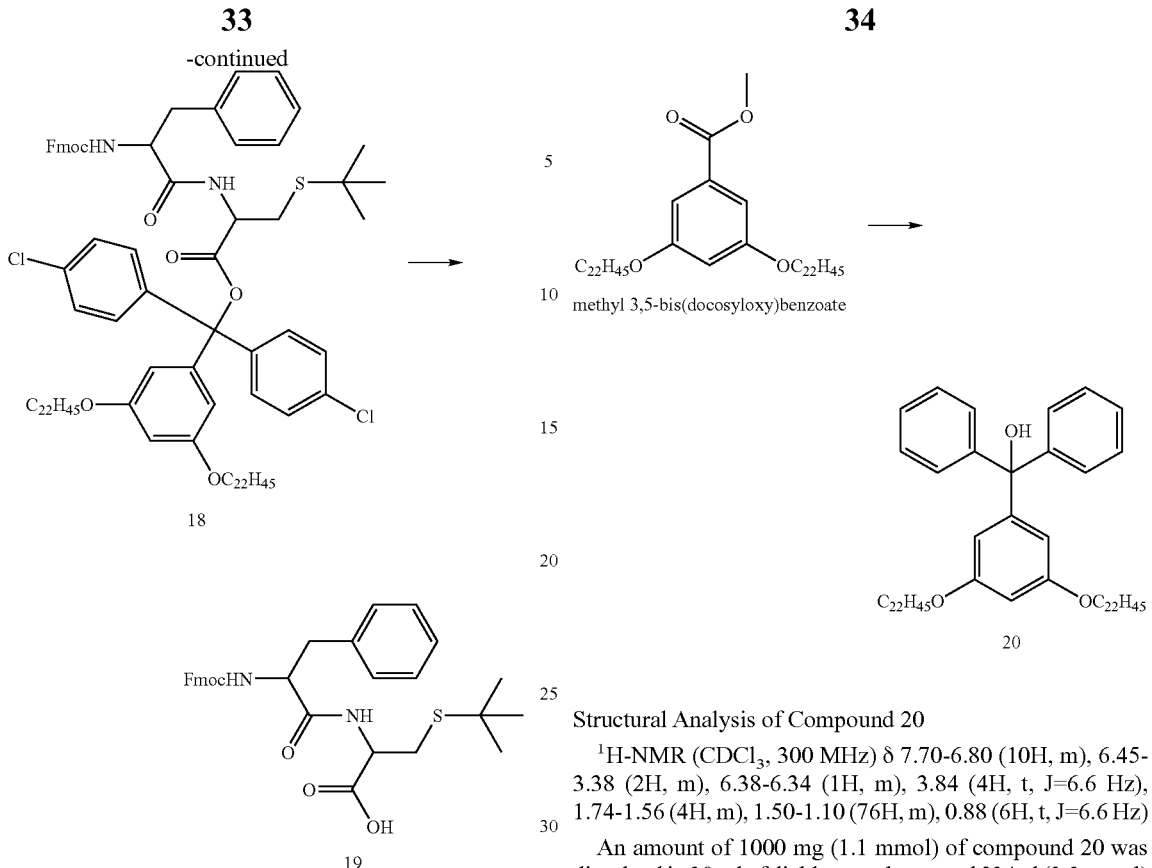

Structural Analysis of Compound 17

$^1$H-NMR (CDCl$_3$, 300 MHz) δ 7.36-7.06 (8H, m), 6.45-6.20 (3H, m), 4.01-3.59 (4H, m), 1.83-1.49 (4H, m), 1.40-1.10 (76H, m), 0.88 (6H, t, J=6.6 Hz)

Structural Analysis of Compound 19

HRMS m/z (ESI) calculated for [M+H]$^+$ 547.2267; found 547.2274

Example 13

Synthesis of Reagent for Organic Synthesis Having a Trityl Group

An amount of 1570 mg (2.0 mmol) of 3,5 bis(docosyloxy) methyl benzoic acid was dissolved in 30 ml of tetrahydrofuran, and 9 ml of a solution of phenylmagnesiumbromide tetrahydrofuran was added and stirring was carried out for 2 hours at 76° C. After confirming the completion of the reaction by thin layer chromatography, 40 ml of 1 N hydrochloric acid was added and the reaction was stopped. After this, extraction was carried out 3 times with 30 ml of hexane, and the extracted organic phase was washed once with 30 ml of 1 N hydrochloric acid, once with a saturated aqueous solution of sodium hydrogen carbonate, and once with a saturated saline solution, and dried with magnesium sulfate. After part of the solution was vacuum distilled, 100 ml of methanol were added to the solution and crystals precipitated, and suction filtration was carried out with a separatory funnel, and 1456 mg of compound 20 were obtained. The yield was 80%. Compound 20; 3,5-bis(docosyloxy)phenyl-diphenyl alcohol

Structural Analysis of Compound 20

$^1$H-NMR (CDCl$_3$, 300 MHz) δ 7.70-6.80 (10H, m), 6.45-3.38 (2H, m), 6.38-6.34 (1H, m), 3.84 (4H, t, J=6.6 Hz), 1.74-1.56 (4H, m), 1.50-1.10 (76H, m), 0.88 (6H, t, J=6.6 Hz)

An amount of 1000 mg (1.1 mmol) of compound 20 was dissolved in 30 ml of dichloromethane, and 234 μl (3.3 mmol) of thionyl chloride was added and reacted for 1 hour at room temperature. After confirming the completion of the reaction by thin layer chromatography, the solvent was vacuum distilled, and a crystalline substance (compound 21) was obtained quantitatively. Compound 21; chloro-3,5-bis(docosyloxy)phenyl-diphenylmethane

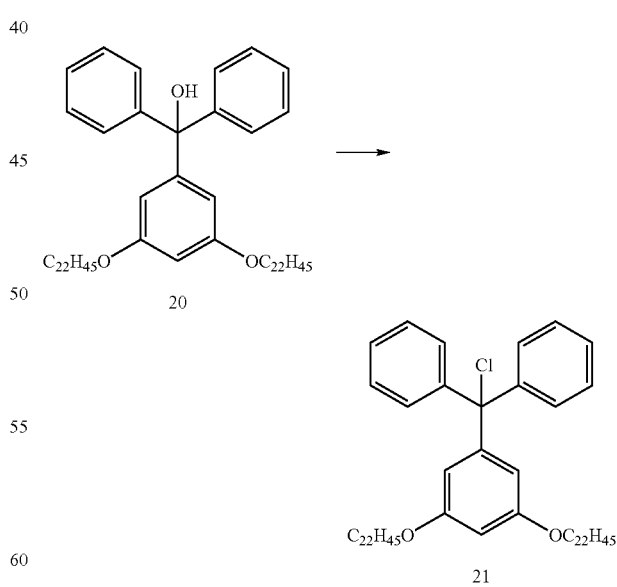

Structural Analysis of Compound 21

$^1$H-NMR (CDCl$_3$, 300 MHz) δ 7.33-7.22 (10H, m), 6.40-6.30 (3H, m), 3.83 (4H, t, J=6.6 Hz), 1.80-1.60 (4H, m), 1.50-1.10 (76H, m), 0.88 (6H, t, J=6.6 Hz)

Example 14

Reaction of Reagent for Organic Synthesis Having a Trityl Group and Amino Acid

An amount of 513 mg (3.3 mmol) of H-Ser-OMe was dissolved in 20 ml of dichloromethane. Then, 1150 μl (6.6 mmol) of diisopropylethylamine was added and in addition, the full amount of compound 21 synthesized in Example 13 was added and stirring was carried out for 30 minutes. After confirming the completion of the reaction by thin layer chromatography, 100 ml of acetonitrile were added, and the dichloromethane was vacuum distilled at room temperature. By carrying out suction filtration on this with a separatory funnel, a crystalline substance (compound 22) was quantitatively obtained. Compound 22; 2-(3,5-bis(docosyloxy)phenyl)-diphenylamino-3-hydroxypropane ethyl ester

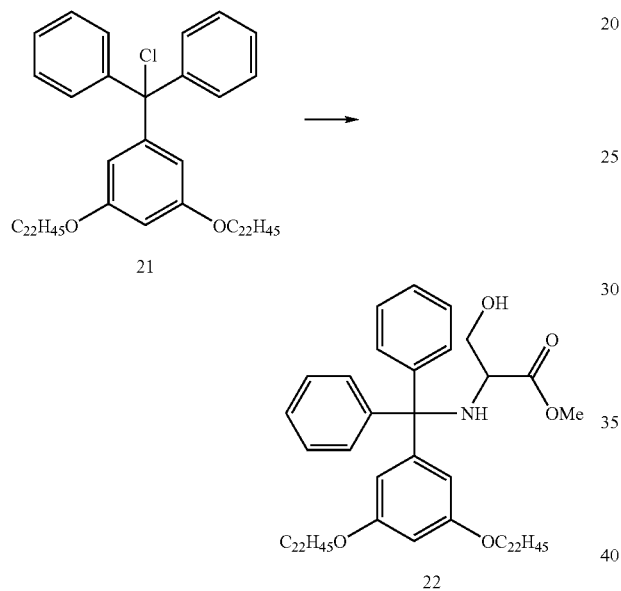

Structural Analysis of Compound 22

$^1$H-NMR (CDCl$_3$, 300 MHz) δ 7.60-7.10 (10H, m), 6.64-6.60 (2H, m), 6.29-6.25 (1H, m), 3.82 (4H, t, J=6.6 Hz), 3.78-3.60 (2H, m), 3.60-3.50 (1H, m), 3.32 (3H, s), 1.74-1.56 (4H, m), 1.50-1.10 (76H, m), 0.88 (6H, t, J=6.6 Hz)

INDUSTRIAL APPLICABILITY

The reagent for organic synthesis and the method of organic synthesis reaction of the present invention make it possible to accelerate the research and development of pharmaceuticals and the like by compound libraries, and in addition contribute to technical innovation in the biochemical and chemical industries. Because the reagent can be efficiently used and recovered, it provides an innovative technology which contributes to the development of "green chemistry".

The invention claimed is:

1. A compound according to Chemical Formula (2):

[Chemical Formula 2]

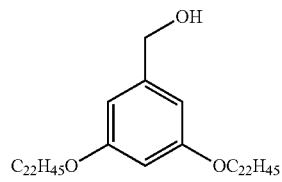

2. A reagent for organic synthesis which can be used for organic synthesis reactions, shown in the following Chemical Formula (1), and having a property of reversibly changing from a liquid phase state to a solid phase state according to changes in at least one selected from the group consisting of solution composition and solution temperature:

[Chemical formula 1]

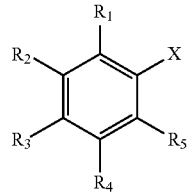

wherein $R_1$, $R_3$ and $R_5$ are hydrogen; and $R_2$ and $R_4$ are alkoxyl groups with a carbon number of 18 to 30 which may have a substituent group, and X represents a reagent active site shown by the following formulas (A), (B), or (O):

—Y—SH       [Formula A]

—Y—NH$_2$   [Formula B]

or

—Y—OH       [Formula O]

wherein, Y is methylene, ethylene or propylene, provided that neither $R_2$ nor $R_4$ is an alkoxyl group with a carbon number of 18 when X is the formula (B) or (O).

3. The reagent for organic synthesis according to claim 2, wherein the reagent active site X in said Chemical Formula (1) is the functional group shown by said formula (O).

* * * * *